United States Patent
Kun

(10) Patent No.: US 6,303,621 B1
(45) Date of Patent: Oct. 16, 2001

(54) METHOD FOR TREATING CANCERS USING A DIIODO THYRONINE ANALOGUE HAVING NO SIGNIFICANT HORMONAL ACTIVITY AND A VINCA ALKALOID AND COMPOSITIONS COMPRISING THE SAME

(75) Inventor: Ernest Kun, Tiburon, CA (US)

(73) Assignee: Octamer, Inc., San Leandro, CA (US)

( * ) Notice: Subject to any disclaimer, the term of this patent is extended or adjusted under 35 U.S.C. 154(b) by 0 days.

(21) Appl. No.: 09/295,662

(22) Filed: Apr. 21, 1999

Related U.S. Application Data

(60) Provisional application No. 60/082,679, filed on Apr. 22, 1998.
(51) Int. Cl.[7] .................. A61K 31/44; A61K 31/235; A61K 31/24
(52) U.S. Cl. .................. 514/283; 514/533; 514/537; 514/543
(58) Field of Search .................. 514/573, 283, 514/533, 537, 543

(56) References Cited

U.S. PATENT DOCUMENTS 5,736,576 * 4/1998 Kun et al. .................. 514/570

OTHER PUBLICATIONS

Carter et al., Chemotherapy of Cancer, Second Edition, John Wiley & Sons, N.Y.,N.Y., p84–5, Aug. 13, 1981.*

* cited by examiner

*Primary Examiner*—Jerome D. Goldberg
(74) *Attorney, Agent, or Firm*—Howrey, Simon, Arnold, & White, LLP; Albert P. Halluin; Viola T. Kung

(57) ABSTRACT

The present invention is directed to a method for treating cancers by administering a pharmaceutically effective amount of a diiodo thyronine analogue having no significant hormonal activity and a vinca alkaloid or biologically active analog thereof. The present invention also features novel pharmaceutical compositions comprising the same.

10 Claims, 7 Drawing Sheets

METHOD FOR TREATING CANCERS USING A DIIODO THYRONINE ANALOGUE HAVING NO SIGNIFICANT HORMONAL ACTIVITY AND A VINCA ALKALOID AND COMPOSITIONS COMPRISING THE SAME

This application claims benefit of provisional application No. 60/082,679 filed Apr. 22, 1998.

The present invention is in the field of biochemistry and pharmacology. Specifically, the present invention relates to methods for treating cancers and malignancies by administering a pharmaceutically effective amount of a diiodo thyronine analogue having no significant hormonal activity and a vinca alkaloid. The invention also relates to pharmaceutical compositions comprising the same.

BACKGROUND OF THE INVENTION

Antineoplastic chemotherapy currently encompasses several groups of drugs including alkylating agents, purine antagonists and antitumor antibiotics. Alkylating agents alkylate cell proteins and nucleic acids preventing cell replication, disrupting cellular metabolism and eventually leading to cell death. Typical alkylating agents are nitrogen mustard, cyclophosphamide and chlorambucil. Toxicities associated with alkylating agents treatment include nausea, vomiting, alopecia, hermorrhagic cystitis, pulmonary fibrosis and an increased risk of developing acute leukemia.

Purine, pyrimidine and folate antagonists are cell cycle and phase specific and, in order to promote an anti-tumor effect, they require cells to be in the cell replication cycle and in the DNA synthesis phase of replication. The purine antagonists such as 6-mercaptorpurine or 6-thioguanidine inhibit de novo purine synthesis and interconversion of purines. The pyrimidine antagonists, such as cytarabine, -fluorouracil or floxuridine inhibit DNA synthesis by inhibiting deoxycytidylate kinase and DNA polymerase.

Folate antagonists, e.g., methotrexates, bind tightly with the intracellular enzyme dihydrofolate reductase ultimately leading to cell death resulting from an inability to synthesize pyrimidines. Toxicities associated with the use of these compounds include alopecia, myelosuppression, vomiting, nausea, and cerebellar ataxia, among others.

Plant alkaloids such as vincristine, vinblastine or podophyllotoxins etoposide and tenisposide generally inhibit mitosis and DNA synthesis and RNA dependent protein synthesis. Toxicities of these drugs are similar to those described above and include myopathy, myelosuppression, peripheral neuropathy, vomiting, nausea and alopecia.

Antitumor antibiotics such as doxorubicin, daunorubicin and actinomycin act as intercalators of DNA, preventing cell replication, inhibiting synthesis of DNA-dependent RNA and inhibiting DNA polymerase. Bleomycin causes scission of DNA and mitomycin acts as inhibitor of DNA synthesis by bifunctional alkylation. Toxicities of these antibiotics are numerous and severe and include necrosis, myelosuppression, anaphylactic reactions, anorexia, dose-dependent cardiotoxicity and pulmonary fibrosis.

Other compounds used for chemotherapeutic treatment of cancer are inorganic ions such as cisplatin, biologic response modifiers such as interferon, enzymes and hormones. All these compounds, similarly to those mentioned above, are accompanied by toxic adverse reactions.

Accordingly, it would be extremely advantageous to provide safe and non-toxic chemotherapeutic compositions which would effectively inhibit and/or suppress tumor cell proliferation and/or neoplastic growth. Furthermore, it would be extremely advantageous to provide safe, effective and non-toxic chemotherapeutic compositions that are easy to administer.

The identification of safe, effective, non-toxic, and orally administrable organic compounds capable of depressing or regressing malignant tumor growth in mammals and the use of such compounds to treat cancer is therefore desirable and the object of this invention.

Several naturally-occurring alkaloids obtained from *Vinca rosea* have demonstrated efficacy in treating malignancies. Examples of these include leurosine, vincaleukoblastine or vinblastine, leuroformine; leurosidine (vinrosidine) and leurocristine or vincristine; deoxy vinblastine "A" and "B"; 4-desacetoxyvinblastine; 4-desacetoxy-3-hydroxyvinblastine; leurocolombine and vincadioline. At least two of these alkaloids, vinblastine and vincristine, are now marketed as drugs for treating malignancies, especially leukemias and related diseases in humans.

Chemical modification of the vinca alkaloids has been relatively limited. Among the successful modifications of physiologically-active alkaloids has been the preparation of dihydro vinblastine and the replacement of the acetyl group at C-4 (carbon no. 4 of the vinblastine ring system) with higher alkanoyl group or with unrelated acyl groups. One of the derivatives in which a chloracetyl group replaced the C-4 acetyl group of vinblastine has been shown to be a useful intermediate for the preparation of structurally modified vinblastine compounds in which an N,N-dialkylglycyl group replaced the C-4 acetyl group of vinblastine. C-3 carboxamide derivatives of vinblastine, vincristine, vincadioline etc. have also been prepared and found to be active anti-tumor agents. Certain of the amide derivatives actually approach the activity of vincristine against these tumors. One of these amides, 4-desacetyl vinblastine C-3 carboxamide or vindesine has been found active in certain leukemias.

SUMMARY OF THE INVENTION

One aspect of the invention is a method for treating cancers and malignancies by administering a pharmaceutically effective amount of a diiodo thyronine analogue having no significant hormonal activity, particularly methyl 3,5-diiodo-4-(4'-methoxy phenoxy) benzoate ("DIME"), 1-[3,5-diiodo-4-(4'-methoxyphenoxy)-phenyl]-ethanone ("DIPE") and [1-3,5-diiodo-4-(4'-methoxyphenoxy)-phenyl]-propanone ("DIPP") and a vinca alkaloid or biologically active analog thereof. The method generally involves administering to a mammal an amount of a diiodo thyronine analogue and a vinca alkaloid effective to depress or regress malignant tumor growth or to treat cancer. The diiodo thyronine analogues typically are characterized as lacking significant hormonal activity.

Yet another aspect of the invention is novel pharmaceutical compositions comprising a pharmaceutically effective amount of a diiodo thyronine analogue having no significant hormonal activity, particularly methyl 3,5-diiodo-4-(4'-methoxy phenoxy) benzoate ("DIME"), 1-[3,5-diiodo-4-(4'-methoxyphenoxy)-phenyl]-ethanone ("DIPE") and 1-[3,5-diiodo-4-(4'-methoxyphenoxy)-phenyl]-propanone ("DIPP") and a vinca alkaloid or biologically active analog thereof.

In one embodiment, diiodo thyronine analogues useful in the methods of the present invention are compounds having the structural formula:

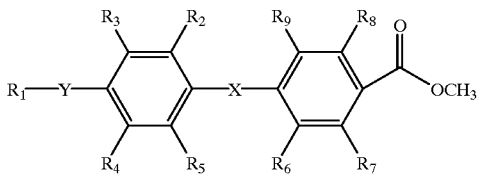

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are each independently selected from the group consisting of: H, $(C_1-C_4)$ alkyl, $(C_1-C_4)$ alkenyl, $(C_1-C_4)$ alkynyl, hydroxy, $(C_1-C_4)$ alkoxy and halogen; and $R_6$, $R_7$, $R_8$ and $R_9$ are each independently selected from the group consisting of: H, $(C_1-C_4)$ alkyl, $(C_1C_4)$ alkenyl, $(C_1-C_4)$ alkynyl, hydroxy, $(C_1-C_4)$ alkoxy, halogen, $NO_2$ and $NH_2$.

In another illustrative embodiment, diiodo thyronine analogues useful in the methods of the present invention are compounds having the structural formula:

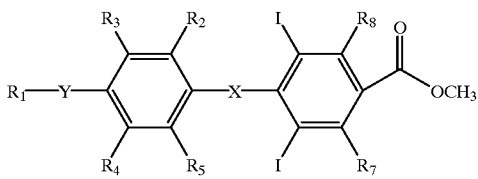

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are each independently selected from the group consisting of: H, $(C_1-C_4)$ alkyl, $(C_1-C_4)$ alkenyl, $(C_1-C_4)$ alkynyl, hydroxy, $(C_1-C_4)$ alkoxy and halogen; and $R_7$ and $R_8$ are each independently selected from the group consisting of: H, $(C_1-C_4)$ alkyl, $(C_1-C_4)$ alkenyl, $(C_1-C_4)$ alkynyl, hydroxy, $(C_1-C_4)$ alkoxy, halogen, $NO_2$ and $NH_2$.

In a preferred embodiment of the invention the diiodo thyronine analogue is methyl 3,5-diiodo-4-(4'-methoxyphenoxy) benzoate ("DIME").

Ketone diiodo thyronine analogues useful in the methods of the present invention are generally compounds having the structural formula:

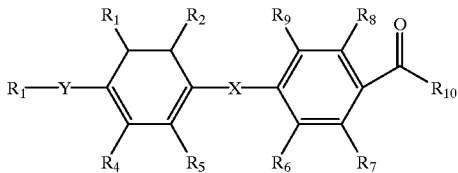

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are each independently selected from the group consisting of: H, $(C_1-C_4)$ alkyl, $(C_1-C_4)$ alkenyl, $(C_1-C_4)$ alkyl, hydroxyl, $((C_{1-C4})$ alkoxy and halogen;

$R_6$, $R_7$, $R_8$ and $R_9$ are each independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy, halogen, $NO_2$, and $NH_2$; and $R_{10}$ is selected from the group consisting of $(C_1-C_4)$ alkyl, $(C_1-C_4)$ alkenyl, and $(C_1-C_4)$ alkynyl.

In a preferred embodiment, compounds useful in the methods of the present invention are compounds having the structural formula:

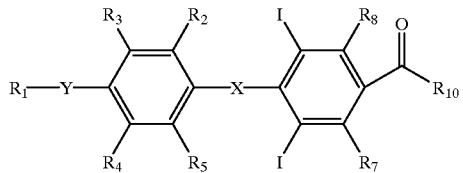

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are each independently selected from the group consisting of: $H_1(C_1-C_4)$ alkyl, $(C_1-C_4)$ alkenyl, $(C_1-C_4)$ alkynyl, hydroxyl, $(C_1-C_4)$ alkoxy and halogen; $R_7$ and $R_8$ are each independently selected from the group consisting of: $H_1$ $(C_1-C_4)$ alkyl, $(C_1-C_4)$ alkenyl, $(C_1-C_4)$ alkynyl, hydroxyl, $(C_1-C_4)$ alkoxy, halogen, $NO_2$ and $NH_2$; and $R_{10}$ is selected from the group consisting of $(C_1-C_4)$ alkyl, $(C_1-C_4)$ alkenyl and $(C_1$ to $C_4)$ alkynyl.

In a particularly preferred embodiment, the compound is selected from the group consisting of 1-[3,5-diiodo-4-(4'-methoxyphenoxy)-phenyl]-ethanone (DIPE) and 1-[3,5-diiodo-4-(4'-methoxyphenoxy)-phenyl]-1-propanone (DIPP).

In preferred embodiments the vinca alkaloid is selected from the group consisting of leurosine, vincaleukoblastine or vinblastine, leuroformine; leurosidine (vinrosidine), leurocristine or vincristine, deoxy vinblastine "A" and "B", 4-desacetoxyvinblastine, 4-desacetoxy-3-hydroxyvinblastine, leurocolombine and vincadioline. In especially preferred embodiments, the vinca alkaloid is vinblastine or vincristine.

Diiodo thyronine analogues and methods of treating cancer using the same are the subject of U.S. Ser. Nos. 08/655,267 and 08/833,272 filed on Jun. 4, 1996 and Apr. 3, 1997 respectively. The disclosure of both applications are herein expressly incorporated by reference in their entirety. Ketone diiodo thyronine analogues are the subject of U.S. Ser. No. 08/956,711 Oct. 23, 1997. The disclosure of this application is also herein expressly incorporated by reference in its entirety.

DETAILED DESCRIPTION OF THE INVENTION

Figure 1:
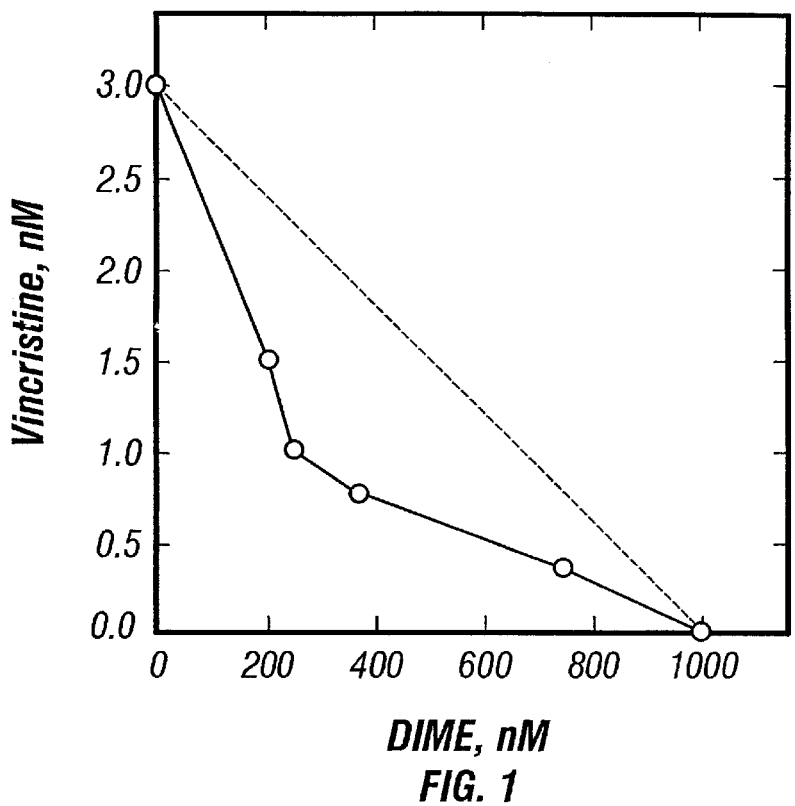
FIG. 1 demonstrates that vinca alkaloids and DIME interact at "mutually exclusive" sites. "Median effect" plots were derived from cell counts after 3 days of exposure to drugs as described by the Methods. $f_v$ is the ratio of the cell count in drug-exposed to that in solvent-exposed cultures. For the mixture of the two drugs (closed circles), 0.75 mM DIME and 2 μM vincristine stock solution were premixed 1:1 and 1 μl of this mixture (or its dilutions at ratios 1:1.5, 1:2, 1:3 or 1:4) was added per 500 p l of culture-mediim in 2 parallel experiments.

The present invention relates to methods of treating malignant tumors and cancer in mammals with analogues of duodo thyronine that are characterized as having no significant hormonal activity in conjunction with a vinca alkaloid or biologically active analog thereof. The present invention is based, in part, on the surprising discovery that certain analogues of thyroxine that do not exhibit hormonal activity are potent, selective and non-toxic inhibitors of malignant tumor growth. The present invention is further based on the surprising discovery that administering an analog of thyroxine together with a vinca alkaloid provides increased inhibition of tumor growth representing more than an additive effect. The preferred diiodo thyronine analogue is referred to herein as DIME.

Thyroxine, an amino acid of the thyroid gland (*Merck Index*, 1989, 9348:1483) and analogues thereof are well-known in the art. It is well established in the literature that thyroid hormones, specifically thyroxine T3 and T4, have two distinct types of biological actions: one on cell metabolism, the second on cell differentiation and development (Jorgensen, 1978, "Thyroid Hormones and Analogues II. Structure-Activity Relationships," In: *Hormonal Proteins and Peptides*, Vol. VI, pp. 107–204, C. H. Li, ed., Academic Press, NY). For example, thyroxine suppresses uptake of iodine by the thyroid (Money et al., 1959, *Endocrinology* 64: 123–125) and induces cell differentiation as studied by tadpole metamorphosis (Money et al., 1958, *Endocrinology* 63:20–28). Additionally, thyroxine and certain analogues thereof depress growth of non-malignant mouse pituitary thyrotropic tumors (Kumaoka et al., 1960, *Endocrinology* 66:32–38; Grinberg et al., 1962, *Cancer Research* 22:835–841).

The structural requirements of thyroxine and thyroxine analogues for metabolic stimulation and induction of cell differentiation are not identical (Jorgensen, 1978, "Thyroid Hormones and Analogues II. Structure-Activity Relationships," In: *Hormonal Proteins and Peptides*, Vol. VI, p. 150, C. H. Li, ed., Academic Press, NY). For example, Money et al., found that there is no correlation between suppression of thyroid iodine uptake and induction of tadpole metamorphosis (Money et al., 1958, *Endocrinology* 63:20–28).

Based on these observations, it was conceived that as yet unidentified cellular responses may be altered or induced by certain diiodo thyronine analogues which do not exhibit either mode of action (metabolic or differentiating) exhibited by thyroxine T3 and T4.

The Diiodo Thyronine Analog Compounds

Diiodo thyronine analogues useful in the methods of the present invention are generally compounds having the structural formula:

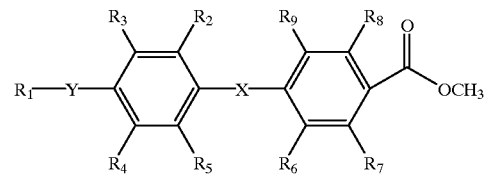

and pharmaceutically acceptable salts thereof, wherein:
$X=O$, $S$, $CH_2$, carboxy or absent;
$Y=O$ or $S$;
$R_1$=methyl or ethyl;
$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen, and
$R_6$, $R_7$, $R_8$ and $R_9$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.

In a preferred embodiment, diiodo thyronine analogues useful in the methods of the present invention are compounds having the structural formula:

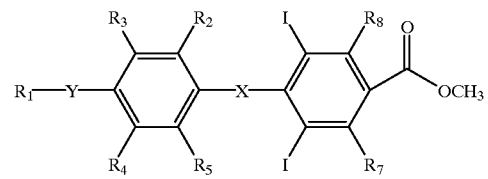

and pharmaceutically acceptable salts thereof, wherein:
$X=O$, $S$, $CH_2$, carboxy or absent;
$Y=O$ or $S$;
$R_1$=methyl or ethyl;
$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen; and $R_7$ and $R_8$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.

In a particularly preferred embodiment, the diiodo thyronine analogue is methyl 3,5-diiodo-4-(4'-methoxyphenoxy) benzoate ("DIME").

Also useful in the compositions and methods of the present invention are ketone diiodo thyronine analogues. Ketone diiodo thyronine analogues useful in the methods of the present invention are generally compounds having the structural formula:

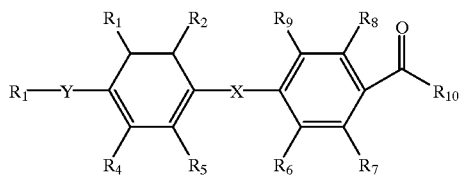

and pharmaceutically acceptable salts thereof, wherein:

$X$=O, S, $CH_2$, carboxy or absent;

$Y$=O or S;

$R_1$=methyl or ethyl;

$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkyl, hydroxyl, (($C_1$–$C_4$) alkoxy and halogen;

$R_6$, $R_7$, $R_8$ and $R_9$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$, and $NH_2$; and $R_{10}$ is selected from the group consisting of ($C_1$–$C_4$) alkyl, ($C_1$–$C_4$) alkenyl, and ($C_1$–$C_4$) alkynyl.

In a preferred embodiment, compounds useful in the methods of the present invention are compounds having the structural formula:

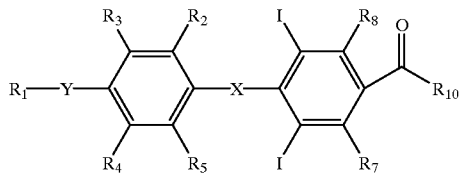

and pharmaceutically acceptable salts thereof, wherein:

$X$=O, S, $CH_2$, carboxy or absent;

$Y$=O or S;

$R_1$=methyl or ethyl;

$R_2$, $R_3$, $R_4$ and $R_5$ are each independently selected from the group consisting of: $H_1$ ($C_1$–$C_4$) alkyl, ($C_1$–$C_4$) alkenyl, ($C_1$–$C_4$) alkynyl, hydroxyl, ($C_1$–$C_4$) alkoxy and halogen; $R_7$ and and $R_8$ are each independently selected from the group consisting of: $H_1$ ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$; and $R_{10}$ is selected from the group consisting of ($C_1$ to $C_4$) alkyl, ($C_1$–$C_4$) alkenyl and ($C_1$ to $C_4$) alkynyl.

In a particularly preferred embodiment, the compound is selected from the group consisting of 1-[3,5-diiodo-4-(4'-methoxyphenoxy)-phenyl]-ethanone (DIPE) and 1-[3,5-diiodo-4-(4'-methoxyphenoxy)-phenyl]-1-propanone (DIPP).

Diiodo thyronine analogues such as DIME have been described in the literature. However, unlike thyroxine, DIME was reported to have no significant metabolic or cell differentiating activity (as determined by tadpole metamorphosis) (Money et al., 1958, *Endocrinology* 63:20–28; Stasilli et al., 1959, *Endocrinology* 64:62–82). For example, uptake of iodine into the thyroid of rats is only marginally (15%) inhibited by DIME as compared to thyroxine (Money et al., 1959, *Endocrinology* 64:123–125). Furthermore, DIME was reported to have no inhibitory activity against the growth of a non-malignant mouse pituitary adenoma (Kumaoka et al., 1960, *Endocrinology* 66:32–38; Grinberg et al., 1962, *Cancer Research* 22:835–841).

It has now been discovered that certain diiodo thyronine analogues having no significant hormonal activity, particularly DIME, not only inhibit the growth of a variety of malignant cell types, but induce tumor cell apoptosis preceded by micronucleation as well. These cytostatic and cytocidal activities are sensitive to structure. Testing of thirteen structural analogues and homologues of DIME indicates that even minor alterations of the methyl ester and 4'-methyoxy substituents renders the molecule completely inactive. Whereas DIME is highly active both in cellular assays and in vivo, the 4'-propoxy and ethyl ester homologues are completely inactive. Accordingly, DIME defines a critical arrangement of molecular moieties, or a pharmacophore, having specific cytostatic and cytocidal activity, and consequently significant chemotherapeutic potential.

While not intending to be bound by theory, it is believed that the most probable molecular mode of action of the diiodo thyronine analogues described herein is cell cycle inhibition and induction of apoptosis.

Progression of eukaryotic cells through the cell division cycle is primarily controlled by the activity of cyclin-dependent protein kinases. The best studied event is the transition from G2 to M phase, which is controlled by cdc2 kinase complexed with cyclin B (for a review see, Dunphy, 1994, *Trends Cell. Biol.* 4:202–207). cdc2 kinase activation requires phosphorylation, a process that is regulated by protein phosphatase 2A (for a review, see, Wera et al., 1995, *Biochem. J.* 311:17–29).

It has been discovered that the diiodo thyronine analogues described herein exert specific activation of protein phosphatase 2A both in vitro and in vivo. In vivo, activation of protein phosphatase 2A coincides with inhibition of cdc2 kinase and dephosphorylation of MAP kinase and topoisomerase II, rendering both of the latter enzymes inactive. DIME has no metabolic action, nor does it inhibit the biosynthetic pathways of DNA, RNA or proteins. Thus, the most probable mode of action is cell cycle inhibition and induction of apoptosis via dephosphorylation of these critical regulatory proteins. Accordingly, activation of phosphatase 2A and concomitant inhibition of cdc2 kinase is an important and powerful therapeutic target 5 for the treatment of cancer.

While alterations at the ester and 4'-positions appear to significantly affect the effectivity of DIME, diiodo thyronine analogues useful for depressing malignant tumor growth and treating cancer are not limited to DIME. For example, the 4'-ethoxy homologue exhibits about 25–30% maximal cytocidal action on human cancer cells as compared to DIME. It is also expected that DIME may be substituted at the aromatic ring positions or bridge oxygen without significant loss of activity.

It is known that the aromatic rings of thyroxine are not contained within the same plane (Jorgensen, 1978, "Thyroid Hormones and Analogues II. Structure-Activity Relationships," In: *Hormonal Proteins and Peptides,* Vol. VI, pp. 107–204, C. H. Li, ea., Academic Press, NY). It is also known that the ring positions of both of the aromatic rings in thyroxine can be substituted with a variety of substituents, including alkyl, halogen, nitro and amino groups with varying degrees of retention of hormonal activity. Id. Furthermore, the ether oxygen connecting the rings can be absent or replaced with a variety of groups or atoms that do not confine the aromatic rings to the same plane, such as, for example, a methylene group, a carboxy group or sulfur, without significant loss of hormonal activity. Id. Accordingly, it is expected and predictable that similar substitutions on DIME will not effect significant loss of anti-cancer activity.

Significantly, the 2'-chloro analogue of DIME exhibited about 25% maximal inhibitory action on the growth of human cancer cells as compared to DIME in studies set forth in U.S. Ser. Nos. 08/655,267 and 08/833,272.

Due to the stringent correlation between in vitro and in vivo efficacy, effective compounds useful in the methods of the invention may be conveniently identified in in vitro assay screening tests. Such tests may screen for the ability of a particular compound to activate protein phosphatase 2A. Typically, compounds useful in the methods of the present invention will increase protein phosphatase 2A activity by a factor of about two to three.

Such tests may also screen for the ability of a particular compound to inhibit malignant tumor cell growth in vitro or in vivo or abolish tumorigenicity of malignant cells. Generally, active compounds useful in the methods of the present invention will exhibit an $I_{50}$ (concentration of compound lethal to 50% of a cell culture as compared to a control culture) in the range of about 0.5 $\mu$m to 5.0 $\mu$m.

As will be appreciated by the skilled artisan, many varieties of malignant tumor cell cultures and cell lines may be used to screen for activity, including but not limited to HL-60, HT-144, E-ras-20, DU-145, MDA-168, MCF-7, 855-2 and MDA-MB-231. Of course, other in vitro and/or in vivo assays as will be apparent to the skilled artisan to screen for anti-tumor and/or anti-cancer activity may also be employed to identify effective diiodo thyronine analogues useful in the present invention.

The chemical formulae referred to herein may exhibit the phenomena of tautomerism or conformational isomerism. As the formulae drawings within this specification can only represent one of the possible tautomeric or conformational isomeric forms, it should be understood that the invention encompasses any tautomeric or conformational isomeric forms which exhibit biological or pharmacological activities similar to DIME, as described herein.

In addition to the above-described compounds and their pharmaceutically acceptable salts, the invention may employ, where applicable, solvated as well as unsolvated forms of the compounds (e.g. hydrated forms).

The compounds described herein may be prepared by any process known to be applicable to the preparation of chemical compounds. Suitable processes are illustrated by the representative examples. Necessary starting materials may be obtained by standard procedures of organic chemistry.

Cancers

The compositions comprising diiodo thyronine analogues and vinca alkaloids described herein are useful for treating a wide variety of cancers. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas.

In a preferred embodiment of the invention, the cancer is associated with the formation of solid tumors including, by way of example and not limitation, mammary and prostatic cancers.

Pharmaceutical Formulations and Routes of Administration

A diiodo thyronine analogues and vinca alkaloids useful in the present invention can be administered to a human patient per se, in the form of a pharmaceutically acceptable salt, or in the form of a pharmaceutical composition where the compound is mixed with suitable carriers or excipient(s) in a therapeutically effective amount, i.e., at doses effective to depress or suppress malignant cell growth or result in amelioration of symptoms associated with cancerous diseases.

Routes Of Administration

The pharmaceutical compositions described herein may be administered by a variety of routes. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than systemic manner, for example via injection of the compound directly into a solid tumor, often in a depot or sustained release formulation.

Furthermore, one may administer the compounds in a targeted drug delivery system, for example, in a liposome coated with tumor-specific antibody. The liposomes will be targeted to and taken up selectively by the tumor.

In a preferred embodiment, the diiodo thyronine analogues and pharmaceutical compositions described herein are administered orally.

Composition/Formulation

The pharmaceutical compositions described herein may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For oral administration, the compounds can be formulated readily by combining with pharmaceutically acceptable carriers that are well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodiim carboxymethylcellulose, and/or polyvinylpyrrolidone (PVP). If desired, disintegrating agents may be added, such as the cross-linked polyvinyl pyrrolidone, agar, or alginic acid or a salt thereof such as sodiim alginate.

Dragee cores are provided with suitable coatings. For this purpose, concentrated sugar solutions may be used, which may optionally contain gum arable, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. The compositions may take such forms as suspensions, solutions or emulsions in oily or aqueous vehicles, and may contain formulatory agents such as suspending, stabilizing and/or dispersing agents.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A suitable pharmaceutical carrier for hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% (w/v) benzyl alcohol, 8% (w/v) of the nonpolar surfactant polysorbate 80, and 65% (w/v) polyethylene glycol 300, made up to volume in absolute ethanol. The VPD co-solvent system (VPD:5W) consists of VPD diluted 1:1 with a 5% (w/v) dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Other formulations suitable for administering the duiodo thyronine analogues described herein will be apparent to those having skill in the art, and may be found, for example, in *Remington's Pharmaceutical Sciences,* Mack Publishing Co., Easton, Pa., latest edition.

Effective Dosages

Pharmaceutical compositions suitable for use in the present invention include compositions wherein the active ingredients are contained in a therapeutically effective amount. Determination of an effective amount is well within the capability of those skilled in the art, especially in light of the detailed disclosure provided herein.

Initial dosages can also be estimated from in vivo data. For example, it has been found that 250 mg/kg of a diiodo thyronine analogue administered by gavage once daily, 5 days a week for 32 days significantly depressed the growth of mammary cancer xenografts (MDA-MB-23 1) in nude mice. Studies have also shown that DIME has a half-life $(t_{1/2})$ in serum of about 2–2.5 hours, and is 87% bioavailable by per os administration (see Example 2.2). One having ordinary skill in the art could readily optimize administration to humans based on this data. The appropriate dosages for vinca alkaloids such as vinblastine and vincristine are well known to those skilled in the art.

Dosage amount and interval may be adjusted individually to provide optimal results. Drug concentration in a solid tumor should be about 2 $\mu$m in most situations.

In cases of local administration or selective uptake, the effective local concentration of the drug may not be related to plasma concentration. One having skill in the art will be able to optimize therapeutically effective local dosages without undue experimentation.

The amount of composition administered will, of course, be dependent on the subject being treated, on the subject's weight, the severity of the affliction, the manner of administration and the judgment of the prescribing physician.

The chemotherapy may be repeated intermittently while tumors are detectable or even when they are not detectable. Moreover, due to the apparent nontoxicity of the compounds used in the present invention, the therapy may be provided alone or in combination with other anti-cancer or other drugs, such as for example AZT, anti-inflammatories, antibiotics, corticosteroids, vitamins and the like.

Toxicity

Toxicity and therapeutic efficacy of the diiodo thyronine analogues and the vinca alkaloids described herein can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. The exact formulation, route of administration and dosage can be chosen by the individual physician in view of the patient's condition. (See, e.g., Ansel et al., 1995, *Pharmaceutical Dosage Forms and Drug Delivery Systems*, $6^{th}$ ed.).

One of the advantages, among others, of using the diiodo thyronine analogues described herein to treat cancer is their lack of toxicity. For example, it has been found that a daily oral dose of 1 g/kg administered for 12–15 days produced no ill effects in nude mice. Since the i.v. serum half-life ($t_{1/2}$) of DIME is about 2–2.5 hours, repeated daily dosages of the diiodo thyronine analogues described herein without ill effects is predictable.

The Vinca Alkaloid Compounds

The methods and compositions of the present invention feature a vinca alkaloid or a biologically active analog thereof. Several vinca alkaloids obtained from *Vinca rosea* have demonstrated efficacy in the treatment of malignancies. Some of these include leurosine (U.S. Pat. No. 3,370,057), vincaleukoblastine or vinblastine (U.S. Pat. No. 3,097,137), leuroformine (Belgian Pat. No. 811,110); leurosidine (vinrosidine) and leurocristine or vincristine (both in U.S. Pat. No. 3,205,220); deoxy vinblastine "A" and "B" *Tetrahedron Letters*, 783 (1958); 4-desacetoxyvinblastine (U.S. Pat. No. 3,954,773); 4-desacetoxy-3-hydroxyvinblastine (U.S. Pat. No. 3,944,554); leurocolombine (U.S. Pat. No. 3,890,325) and vincadioline (U.S. Pat. No. 3,887,565). At least two of these alkaloids, vinblastine and vincristine, are now marketed as drugs for treating malignancies, especially leukemias and related diseases in humans. Vincristine has usually been thought of as the most active and useful agent in the treatment of leukemias but is also the least abundant of the anti-neoplastic alkaloids of *Vinca rosea*. The two marketed alkaloids are customarily administered by the intravenous route.

Chemical modification of the vinca alkaloids has been relatively limited. Among the successful modifications of physiologically-active alkaloids has been the preparation of dihydro vinblastine (U.S. Pat. No. 3,352,868) and the replacement of the acetyl group at C-4 (carbon no. 4 of the vinblastine ring system) with higher alkanoyl group or with unrelated acyl groups. (U.S. Pat. No. 3,392,173). One of the derivatives in which a chloracetyl group replaced the C-4 acetyl group of vinblastine has been shown to be a useful intermediate for the preparation of structurally modified vinblastine compounds in which an N,N-dialkylglycyl group replaced the C-4 acetyl group of vinblastine (U.S. Pat. No. 3,387,001). C-3 carboxamide derivatives of vinblastine, vincristine, vincadioline etc. have also been prepared and found to be active anti-tumor agents. (Belgian Pat. No. 813,168.) Certain of the amide derivatives actually approach the activity of vincristine against these tumors. One of these amides, 4-desacetyl vinblastine C-3 carboxamide or vindesine has been found active in certain leukemias. In humans, vindesine appears to have less neurotoxicity than does vincristine.

Certain vinca alkaloid derivatives are described by, e.g. Miller et al., U.S. Pat. No. 4,160,767 and U.S. Reissue No. 30,561, the disclosures of which are herein incorporated by reference. Additional compounds featuring transferrin coupled to vinca alkaloids are disclosed by Ades et al., U.S. Pat. No. 4,522,750, and certain hydrazine succinimide derivatives of vinca alkaloids are disclosed by Cullinan et al., U.S. Pat. No. 4,667,030, the disclosures of which are herein incorporated by reference. Compounds which are functional analogs of naturally-occurring vinca alkaloids and which retain substantial antineoplastic and/or anti-viral and/or anti-inflammatory are specifically contemplated within the scope of this invention.

Definitions:

"Alkyl" refers to a saturated branched, straight chain or cyclic hydrocarbon radical. Typical alkyl groups include methyl, ethyl, propyl, isopropyl, cyclopropyl, butyl, isobutyl, cyclobutyl, tert-butyl, pentyl, hexyl and the like.

"Alkenyl" refers to an unsaturated branched, straight chain or cyclic hydrocarbon radical having at least one carbon-carbon double bond. The radical may be in either the cis or trans conformation about the double bond(s). Typical alkenyl groups include ethenyl, propenyl, isopropenyl, cyclopropenyl, butenyl, isobutenyl, cyclobutenyl, tert-butenyl, pentenyl, hexenyl and the like.

"Alkynyl" refers to an unsaturated branched, straight chain or cyclic hydrocarbon radical having at least one carbon-carbon triple bond. Typical alkynyl groups include ethynyl, propynyl, butynyl, isobutynyl, pentynyl, hexynyl and the like.

"Alkoxy" refers to an -OR radical, where R is alkyl, alkenyl or alkynyl, as defined above.

"Halogen" generally refers to fluoro, chloro, bromo and iodo substituents. However, as used herein it preferably refers to iodo.

"Mammal" refers to animals or humans.

"Therapeutically effective amount" refers to an amount of a compound or composition effective to depress, suppress or regress malignant cell growth or result in amelioration of symptoms associated with cancerous diseases.

"Duiodo thyronine analog" as used herein refers to both the duodo thyronine analogs defined herein and to the ketone analogs of the same defined herein. Specific exemplary diiodo thyronine analogs include DIME, DIPE and DIPP. The compounds included within the meaning of the term have structural similarity to thyroxine.

"Vinca alkaloid" refers to the naturally-occurring alkaloids obtainable from Vinca rosea that possess anti-cancer, anti-inflammatory or anti-viral properties. The term also encompasses functional analogs including structurally similar compounds having one or more additions, substitutions or deletions whether obtained naturally or synthetically. Such compounds may be obtained or synthesized by those skilled in the art without undue experimentation.

Potentiation and Synergism of Diiodo Thyronine Analogs and Vinca Alkaloids

In order to demonstrate the present invention, the cellular interaction of vinca alkaloids with DIME and DIPE was studied. The data presented herein demonstrate that the apparent drug effects and their interaction are most probably the expression of rate limiting enzymatic and/or regulatory reactions of multicomponent systems that are directly or indirectly modified by ligands. These data demonstrate that vinca alkaloids and DIME interact at "mutually exclusive" sites, thus fulfilling requirements that validate the isobologram method (Chou et al. (1977), Chou et al. (1981) and Chou et al.(1984)). An apparent synergism was demonstrated (FIG. 2) if $I_{50}$ doses of both drugs are applied alone and in combination. When the ratio of drugs was varied and with 0.75 μM DIME (or DIPE) combined with 1–2 nM vincristine, drug concentrations which by themselves do not elicit effects that exceed the SD of average cell growth rates, a very large cooperative action is evident (FIG. 3a,b). These data indicate significant chemotherapeutic potential for administering both drugs concurrently. DIME is a remarkably nontoxic molecule and may be administered p.o. as needed to reach about 0.75 μM concentration in tumor cells. At a concentration of 1–2 nM, vincristine is no more than one tenth of the customarily administered dose discussed the previous literature and thus is probably well tolerated. Consequently, this drug combination demonstrates powerful antitumor action.

Since it has been shown experimentally that DIME or DIPE bind to microtubules as so do the vinca alkaloids, it is reasonable that "mutually exclusive" cellular sites identified herein by kinetics represent tubulin binding. The $K_D$ of DIME vs tubulin is in the order of $1-1.4 \times 10^{-5}$ M and that of vincristine may be a thousand-fold higher (Microtubules, Wiley-Liss Publications, John Wiley and Sons Inc., NY (1994)), consequently the two ligands may bind proportionally to cellular microtubules. However, the intracellular consequences of ligand-binding site interactions on microtubules may be quantitatively different for both drugs alone or in combination. For example the activation mechanisms of caspase 3, essential to induce apoptosis, could be cooperatively influenced by both ligands. It is presently unknown how microtubules may be involved in the regulation of above outlined apoptotic pathways. It has been reported that vinca alkaloids can activate the JNK pathway, MEKK1/SEK1 and c-Jun/AP-1 (Osborn et al. Proc. Amer. Assoc. for Cancer Res. 177, Abstr. No. 1213 (1988)) reactions which lead to apoptosis, possibly via caspase 3. Results shown herein demonstrate a strong correlation between growth inhibition and apoptosis induction via caspase 3. It has been reported that microtubule-reactive drugs, taxol and vinca alkaloids can activate both Ras and apoptosis-regulating kineses (ASK1), pathways (Wang et al. J. Biol. Chem. 273: 4928–4936, (1998)) presumably leading to Bcl-2-regulated apoptosis.

DIME tolerance coincides with a significant decrease of drug permeation, reminiscent of nontumor cells which are impermeable to DIME. Hence the DIME-tolerant cells may represent a transition towards a normal phenotype. A decrease in DIME permeation does not depend on drug exposure but is a phenotypic characteristic of a few percent of the cancer cell population. Whereas doubling time of the cancer cells is 20 hrs, DIME-tolerant cells in the presence of 1.5 μM DIME divide between 70–78 hrs. Removal of DIME shortens doubling time to 40–45 hrs.

EXAMPLES OF THE PREFERRED EMBODIMENTS

The following examples serve to illustrate the invention. They are not intended to be limiting, and those skilled in the art will readily understand that the invention is limited only by the appended claims.

EXAMPLE 1

Synthesis of Diiodo thyronine Analogues

The following examples serve to illustrate the invention. They should not be construed as narrowing it, or limiting its scope.

Fourteen diiodo thyronine analogues were synthesized, purified and characterized. A summary of the structure of each synthesized compound and select physical data is provided at 5 Table 1, below.

TABLE 1

Diiodo thyronine Analogues Synthesized

| No. | $R_1$ | $R_2$ | $R_3$ | $R_4$ | m.p.(° C.) | Formula | Mass (calcd.) | Mass (found) |
|---|---|---|---|---|---|---|---|---|
| 1 | $CH_3O$ | $CH_3O$ | H | H | 153–155 | $C_{15}H_{12}I_2O_4$ | 509.882513 | 509.882960 |
| 2 | EtO | $CH_3O$ | H | H | 123–125 | $C_{16}H_{14}I_2O_4$ | 523.898163 | 523.898737 |
| 3 | n-PrO | $CH_3O$ | H | H | 114–116 | $C_{17}H_{16}I_2O_4$ | 537.913813 | 537.914014 |
| 4 | n-BuO | $CH_3O$ | H | H | 82–84 | $C_{18}H_{18}I_2O_4$ | 551.929463 | 551.930000 |
| 5 | $CH_3O$ | EtO | H | H | 96–98 | $C_{16}H_{14}I_2O_4$ | 523.898163 | 523.898202 |
| 6 | $CH_3O$ | HO | H | H | 233–235 | $C_{14}H_{10}I_2O_4$ | ref[a] | |
| 7 | $CH_3O$ | $H_2N$ | H | H | 207–209 | $C_{14}H_{11}I_2NO_3$ | 494.882847 | 494.881880 |
| 8 | $CH_3O$ | $(CH_3)HN$ | H | H | 181–183 | $C_{15}H_{13}I_2NO_3$ | 508.898497 | 508.898971 |
| 9 | $CH_3O$ | $(CH_3)_2N$ | H | H | 162–164 | $C_{16}H_{15}I_2NO_3$ | 522.914148 | 522.914364 |
| 10 | HO | $CH_3O$ | H | H | 204 (dec.)[b] | $C_{14}H_{10}I_2O_4$ | 495.866863 | 495.867453 |
| 11 | H | $CH_3O$ | H | H | 142–144 | $C_{14}H_{10}I_2O_3$ | 479.871948 | 479.872553 |
| 12 | I | $CH_3O$ | H | H | 139–141 | $C_{14}H_9I_3O_3$ | 605.768600 | 605.767839 |
| 13 | H | $CH_3O$ | H | $CH_3O$ | 123–125 | $C_{15}H_{12}I_2O_4$ | 509.882513 | 509.882387 |
| 14 | $CH_3O$ | $CH_3O$ | Cl | H | 132–134 | $C_{15}H_{11}ClI_2O_4$ | 543.843541 | 543.843424 | ref[a]Compound 6 was prepared according to Borrows et al, J. Chem. Soc. 1949:S185–S190.
[b]Decomposition temperature.

1.5 Ethyl 3,5-diiodo-4-(4'-methoxyphenoxy) benzoate (Compound 5)

Ethyl 3,5-diiodo-4-(4'-methoxyphenoxy)benzoate (Compound 5) was synthesized by way of 3,5-diiodo-4-(4'-methoxyphenoxy) benzoyl chloride, the latter having been described in Borrows et al., supra. Thus, in a 10 ml flask 3,5-diiodo-4-(4'methoxyphenoxy)benzoic acid (99.2 mg, 0.200 mmole) was converted to 3,5-diiodo-4-(4'-methoxyphenoxy) benzoyl chloride. After removal of excess thionyl chloride under vacuum, anhydrous ethanol (5.0 ml) was added with stirring and the mixture heated to 70° C. for 5 minutes. Excess ethanol was removed and the dry residue dissolved in hot 95% ethanol (4.0 ml), from which the product ester crystallized in the refrigerator (3° C.). Yield: 55.8 mg (53%) of buff-colored crystals. Melting point: 96–98° C.

Mass spectrum (EI): High-resolution data for the M+peak: calculated for $C_{16}H_{14}I_2O_4$, 523.898163; found, 523.898202 (deviation=–0.1 ppm).

$^1$H NMR spectrum in DMSO-d6 (6 (ppm) values relative to TMS): 1.336 (3H, triplet, J=7.19 Hz), 3.717 (3H, singlet), 4.336 (2H, quartet, J=7.06 Hz), 6.695 (2H, doublet, J=9.34 Hz, plus fine-splitting), 6.895 (2H, doublet, J=9.20, plus fine-splitting), 8.389 (2H, singlet).

1.6 3.5-diiodo-4-(4'-methoxyhenoxy)benzoic acid (Compound 6)

3,5-diiodo-4-(4'-methoxyphenoxy)benzoic acid (Compound 6) was synthesized as described in Borrows et al., supra.

1.7 3,5-diiodo-4-(4'-methoxvphenoxy)benzamide (Compound 7)

3,5-diiodo-4-(4'-methoxyphenoxy)benzamide (Compound 7) was synthesized by amidating Compound 1. In a 125 ml flask, methyl 3,5-diiodo-4-(4'-methoxyphenoxy) benzoate (Compound 1) (100 mg, 0.196 mmole) was dissolved in anhydrous methanol (60 ml). Anhydrous ammonia gas was bubbled into the solution for 5 minutes at a moderate rate at ambient temperature. After standing for 1 hour in the stoppered flask, the ammonia gas treatment was repeated (5 minutes) and the mixture allow to stand in the stoppered flask for 48 hours. The methanol/ammonia was removed by rotary evaporation, the dry residue dissolved in methanol: wafer (7:3 v/v) (30 ml) and crystallized in the refrigerator (3° C.). Yield: 58.3 mg (60% yield) of buff-colored crystals. Melting point: 207–209° C.

Mass spectrum (FAB): High-resolution data for the M+peak: calculated for $C_{14}H_{11}I_2NO_3$, 494.882847; found, 494.881880 (deviation=2.0 ppm).

$^1$H NMR spectrum in DMSO-$d_6$ (6 (ppm) values relative to TMS): 3.716 (3H, singlet), 6.682 (2H, doublet, J=8.93 Hz), 6.895 (2H, doublet, J=8.99 Hz), 7.528 (1H, singlet), 8.113 (1H, singlet), 8.402 (2H, singlet).

1.8 5-diiodo-4-(4'-methoxYphenoxy)-N-methyl benzamide (Compound 8)

3,5-diiodo-4-(4'-methoxyphenoxy)-N-methyl benzamide (Compound 8) was prepared by way of 3,5-diiodo-4-(4'-methoxyphenoxy)benzoyl chloride (see, Example 1.5). The acid chloride was reacted with excess methylamine in tetrahydrofuran at ambient temperature (1 hour), filtered to remove methylamine-hydrochloride precipitate, the solvent 5 evaporated and the product crystallized from 95% ethanol.

1.9 3,5-diiodo-4-(4'-methoxyPhenoxy)-N N-dimethyl benzamide (Compound 9)

3,5-diiodo-4-(4'-methoxyphenoxy)-N,N-dimethyl benzamide (Compound 9) was prepared way of 3,5-diiodo-4-(4'-methoxyphenoxy)benzoyl chloride (see, Example 1.5). The acid chloride was reacted with excess dimethylamine in tetrahydrofuran at ambient temperature (1 hour), filtered to remove dimethylamine-hydrochloride precipitate, the solvent evaporated and the product crystallized from absolute ethanol.

1.10 Methyl 3,5-diiodo-4-(4'-hydroxyphenoxy) benzoate (Compound 10)

Methyl 3,5-diiodo-4-(4'-hydroxyphenoxy) benzoate (Compound 10) was prepared as described in Example 1.2. The dinitro precursor was prepared by reacting 4-chloro-3,5-25 dinitrobenzoate with hydroquinone in pyridine solution as described in Borrows et al., supra.

1.11 Methyl 3.5-diiodo-4-phenoxybenzoate (Compound 11)

Methyl 3,5-diiodo-4-phenoxybenzoate (Compound 11l) was prepared as described in Example 1.2. The dinitro 35 precursor was synthesized by treating an aqueous solution of potassium phenolate (prepared from commercial phenol) with methyl 4-chloro-3,5-dinitrobenzoate. The dinitro product was reduced by $H_2$/Pd(C) to the diamine derivative' which was then tetrazotized with $NaNO_2/H_2SO_4$ and converted to the diiodo product by reaction with potassium iodide (Sandmeyer reaction). Purification was by preparative TLC and crystallization.

1.12 Methyl 3,5-diiodo-4-(4'-iodophenoxy)benzoate (Compound 12)

Methyl 3,5-diiodo-4-(4'-iodophenoxy)benzoate (Compound 12) was synthesized as described in Example 1.2. Since the iodo-substituent in the dinitro precursor is itself labile with respect to reduction by $H_2$/Pd(C), the iodo-dinitro precursor was reduced to the iodo-diamine with iron powder in acetic acid/95% ethanol (see, e.g., Gemmill et al., 1956, *J. Am. Chem. Soc.* 78:2434–2436). The iodo-diamine was then tetrazotized and converted to the triiodo product using the Sandmeyer reaction. After purification by preparative TLC, the product (m.p. 139–141° C.) was crystallized from ethanol.

Mass spectrum (EI): High resolution data for the M+ peak: calculated for C14H,O313, 605.768600; found, 605.767839 (deviation=1.3 ppm).

$^1$H NMR spectrum in DMSO-d6 (6(ppm) values relative to TMS): 3.879 (3H, singlet), 6.628 (2H, doublet, J=8.97 Hz plus fine-splitting), 7.670 (2H, doublet, J=9.12 Hz plus fine-splitting 8.396 (2H, singlet).

1.13 Methyl 3,5-diiodo-4-(3'-methoxphhenoxy) benzoate (Compound 13)

Methyl 3,5-diiodo-4-(3'-methoxyphenoxy)benzoate (Compound 13) was synthesized as described in Example 1.2. The dinitro precursor was synthesized by treating an aqueous solution of potassium 3-methoxy phenolate (prepared from commercial 3-methoxyphenol) with methyl 4-chloro-3,5-dinitrobenzoate. The dinitro product was reduced by $H_2$/Pd(C) to the diamine derivative, which was then tetrazotized with $NaNO_2/H_2SO_4$ and converted to the diiodo product by reaction with potassium iodide (Sandmeyer reaction). Purification was by preparative TLC and crystallization.

1.14 Methyl 3 5-diiodo-4-(2'-chloro-4'-methoxylhenoxy)benzoate (Compound 14)

Methyl 3,5-diiodo-4-(2'-chloro-4'methoxyphenoxy) benzoate (Compound 14) was synthesized by the general methodology described in Example 1.2, but with an alternate method for the reduction of the dinitro precursor.

1.14.1 Methyl 3,5-dinitro-4-(2'-chloro-4'-methoxyphenoxy)benzoate

The dinitro precursor was prepared by reacting 2-chloro-4-methoxyphenol (Aldrich Chemical Co., Milwaukee, Wis.) as the potassium 2-chloro-4-methoxyphenolate with methyl 4-chloro-3,5-dinitrobenzoate, as described in Example 1.2.1. The methyl 3,5-dinitro-4-(2'-chloro-4'-methoxyphenoxy)benzoate product (66% yield) was crystallized from ethanol to give orange crystals. Melting point: 116–119° C.

Mass Spectrum (EI): M+ in high resolution: calculated for C1sHl1c1N2o8, 382.020393; found, 382.020187 (deviation=0.5 2 ppm).

1.14.2 Methyl 3,5-diiodo-4-(2'-chloro-4'-methoxyphenoxy)benzoate

Since the 2'-chloro substituent in the 25 dinitro precursor is labile with respect to reduction by $H_2$/Pd(C), the precursor was reduced to the 2'-chloro diamine with iron powder in acetic acid/95% ethanol, similarly to Example 1.12. Thus, in a 250 ml flask methyl 3,5-dinitro-4(2'-chloro-4'-methoxyphenoxy)benzoate (765.5 mg, 2.00 mmol) 30 was dissolved in glacial acetic acid (35 mL) and 95% ethanol (35 mL), the solution heated to 70° C. and iron powder added (2.00 g). The mixture was vigorously swirled in a heating bath (70° C.). After 3 min. of swirling, the mixture developed a brown color. Swirling was continued at 70° C. for 35 min. The mixture was then transferred to a separatory funnel, water (250 mL) and ethyl acetate (250 mL) were added, the product extracted into the ethyl acetate layer, and the ethyl acetate phase allowed to separate from the aqueous phase (3 hours). The extract was dried over anhydrous $Na_2SO_4$, filtered and the ethyl acetate removed by rotary evaporation to yield the crude 3,5-diamino product, which solidified.

The crude diamino product was immediately dissolved in glacial acetic acid (6.0 mL), tetrazotized and converted via the Sandmeyer reaction to methyl 3,5-diiodo-4-(2'-chloro-4'-methoxyphenoxy)benzoate as described in Example 1.2. After purification by preparative thin layer chromatography (Rf=0.70) as described in Example 1.2, the product was crystallized from 95% ethanol (250.8 mg off-white crystals, 23% yield). Melting point: 132–134° C.

Mass spectrum: EI, m/z (relative intensity): 546 (34), 545 (16), 544 (M+, 100), 418 (6), 382 (6). High resolution data for the M+ peak: calculated for C1sHllC1I2O4, 543.843541; found, 543.843424 (deviation=0.2 ppm).

$^1$H NMR spectrum in DMSO-D6 (S(ppm) values relative to TMS): 3.747 (3H, singlet), 3.881 (3H, singlet), 6.328 (1H, doublet, J=8.97 Hz), 6.780 (1H, doublet of doublets, J=9.10 Hz and J=2.95 Hz), 7.195 (1H, doublet, J=3.02 Hz), 8.400 (2H, singlet).

1.15 Other Compounds

Additional diiodo thyronine analogues described herein can be synthesized using the above-described syntheses from appropriate starting materials, as will be readily apparent to those having skill in the art of organic chemistry. Additional guidance can be found in the art, particularly in Borrows et al., supra; Clayton et al., 1951, *J. Chem. Soc.* 1951:2467–2473; Gemmill et al., 1956, *J. Am. Chem. Soc.* 78:2434–2436; Meltzer et al., 1957, *J. Orq. Chem.* 22:1577–1581; Crowder et al., 1958, *J. Chem. Soc.* 1958:2142–2149; Jorgensen, 1978, "Thyroid Hormones and Analogues, I. Synthesis, Physical Properties and Theoretical Calculations" In: *Hormonal Proteins and Peptides* Vol. VI, pp. 57–105, C. H. Li, Ed., Academic Press, NY (and references cited therein); and Jorgensen, 1978, "Thyroid Hormones and Analogues, II. Structure-Activity Relationships," In: *Hormonal Proteins and Peptides,* Vol. VI, pp. 107–204, C. H. Li, Ed., Academic Press, NY (and references cited therein).

Eample 2
In Vivo Experiments using Diiodo Thyronine Analogues

The following examples demonstrate the non-toxicity, bioavailability, serum half-life (tx) and in vivo efficacy of DIME in treating human mammary cancer xenografts in mice.

Toxicity

Ten nude mice were administered a daily oral dose of $^{14}$C-labeled DIME (Compound 1) (1.0 g/kg, 0.1 mL in corn oil) for a period of 12–15 days. No ill effects were observed in any of the mice during the entire time of treatment.

Serum Half-Life (t½) and Bioavailability

Mice were orally dosed with 126 mg/kg 14C-labeled DIME (Compound 1). After dosing, blood sampling times were 15 and 30 minutes and 1, 2, 4, 6, 8 and 24 hours. Aliquots (50 µL) of blood were assayed in a liquid scintillation counter and data expressed as microgram-equivalents per mL.

The blood level data were analyzed by the RSTRIP method (Micromath, Salt Lake City, Utah). Parallel groups of mice were dosed intravenously with 24.5 mg/kg 14C-labeled DIME and blood sampling times were 10, 20 and 30 minutes and 1, 2, 4, 6 and 8 hours. The compound was determined to demonstrate about 85–90% bioavailability.

Results

The blood serum levels of 14C-labeled DIME (mg-eq./mL) were compared. The area under the blood concentration-time curve was 665.28 µg-hr./mL for the oral route (data represented by circles) and 156 µg-hr/mL for the intravenous route (data represented by squares). Bioavailability of orally administered DIME was calculated to be 83% from these data using a standard ratio×dose method. DIME half-life (t½) was about 2–2.5 hours.

In Vivo Efficacy

The ability of human tumors to grow as xenografts in athymic mice (e.g., nude mice) provides a useful in vivo model for studying the biological response to therapies for human tumors. Since the first successful xenotransplantation of human tumors into athymic mice (Rygaard et al., 1969, *Acta Pathol. Microbial. Scand.* 77:758–760), many different human tumor cell lines (e.g., mammary, lung, genitourinary, gastrointestinal, head and neck, glioblastoma, bone and malignant melanomas) have been successfully transplanted and grown into nude mice. Human mammary tumor cell lines, including MCF-7, ZR75-1 and MDA-MB- 231, have been established as subcutaneous grafts in nude mice (Warri et al., 1991, *Intl. J. Cancer* 49:616–23; Ozzello et al., 1980, *Eur. J. Cancer* 16:553–559; Osbourne et al., 1985, *Cancer Res.* 45:584–590; Siebert et al., 1983, *Cancer Res.* 43:2223–2239).

This experiment demonstrates inhibition of MDA-MB-231 xenografts in nude mice.

Experimental Protocol

MDA-MB-231 (human mammary cancer) cells were obtained from American Type Culture Collection (Rockville, Md.) and maintained in the recommended growth media. Twenty nude mice were each inoculated subcutaneously with MDA-MB-231 cells (106 cells/100 pL). To one group often mice, DIME was administered by gavage (250 mg/kg, 10 mL/kg in corn oil) once 5 per day, 5 days per week, for a total of 32 days. The other (control) group of ten mice was given administered vehicle only according to the same dosing schedule. Tumors were measured twice weekly using a Vernier caliper, and the mean tumor volume was determined at each time point. Comparisons between groups were made using an unpaired, two-tailed t-test and the results were analyzed using analysis of variance.

Results

The average tumor mass at days 14, 21, 28 and 32 post-inoculation for treated and untreated mice is tabulated in Table 2.

TABLE 2

MDA-MB-231 Tumor Volume After DIME Treatment

| Treatment group | Day 14 ± SEM[a] (p value) | Day 21 ± SEM[a] (p value) | Day 28 ± SEM[a] (p value) | Day 32 ± SEM[a] (p value) |
| --- | --- | --- | --- | --- |
| Control (vehicle) | 284.6 ± 42.0 | 622.2 ± 58.1 | 979.0 ± 154 | 1176.6 ± 222.4 |
| DIME (250 MG/KG) | 172.0 ± 34.3 (p = 0.06) | 285.7 ± 62.4 (p = 0.02) | 430 ± 85.6 (p = 0.01) | 543.8 ± 122.1 (p = 0.01) |
| % decrease | 40% | 54% | 56% | 54% |

[a]SEM = standard error of the mean

These data indicate that DIME effects significant reduction of malignant tumor growth, even under a non-optimized treatment regimen.

In vivo Efficacy

Other diiodo thyronine analogues described herein are tested as described above. The analogues are expected to exhibit activity according to these assays.

Example 3

Potentiation and Synergism of Diiodo Thyronine Analogues and Vinca Alkaloids

Methods and Materials a. Chemicals. Vincristine and vinblastine were obtained as sulfates from Sigma Co. and stock solutions prepared in absolute ethnol and dilutions into DMSO. All other reagents were of analytical grade b. Preparation of 1-[3,5-diiodo-4-(4'-methoxyphenoxy)-phenyl]-ethanone (DIPE). Dimethylcadmium (0.50 mmol) was prepared by combining 0.50 mmol of anhydrous cadmium chloride and 1.00 mmol of methylmagnesium bromide (Aldrich Chemical Company, Milwaukee, Wis.) in anhydrous diethyl ether (2.0 ml) following general literature methodology for organocadmium reagents (Kun et al. U.S. Ser. No. 08/956,711 filed on Oct. 23, 1997) and Cason Chem. Rev. 40: 15–32 (1947)). To the preparation was added at ambient temperature a solution of 3,5-diiodo-4-(4'-methoxyphenoxy)-benzoyl chloride (20) (0.20 mmol) in benzene (1.50 ml), and the mixture was stirred for 1 hr. Then ethyl acetate (10 ml) and 0.2 M HCl (10 ml) were added, and the product was extracted into ethyl acetate. Rotatory evaporation gave a viscous residue that slowly solidified. Recrystallization twice from ethanol gave 40.5 mg (40.9% yield) of off-white crystals, m.p. 136–138° C. (literature m.p. 138–143° C. (Dibbo et al. *J. Chem. Soc.* 2890–2902, (1961)).

Mass spectrum: Low-resolution EI, m/z (relative intensity): 494 ($M^+$, 100), 495 (M+1, 20.8), 479 (22.4), 309 (5.9), 239 (4.5), 225 (7.5). High-resolution data from the $M^+$ peak: calculated for $C_{15}H_{12}O_3I_2$, 493.887598; found, 493.888689 (deviation=−2.2 ppm).

Figure 8:
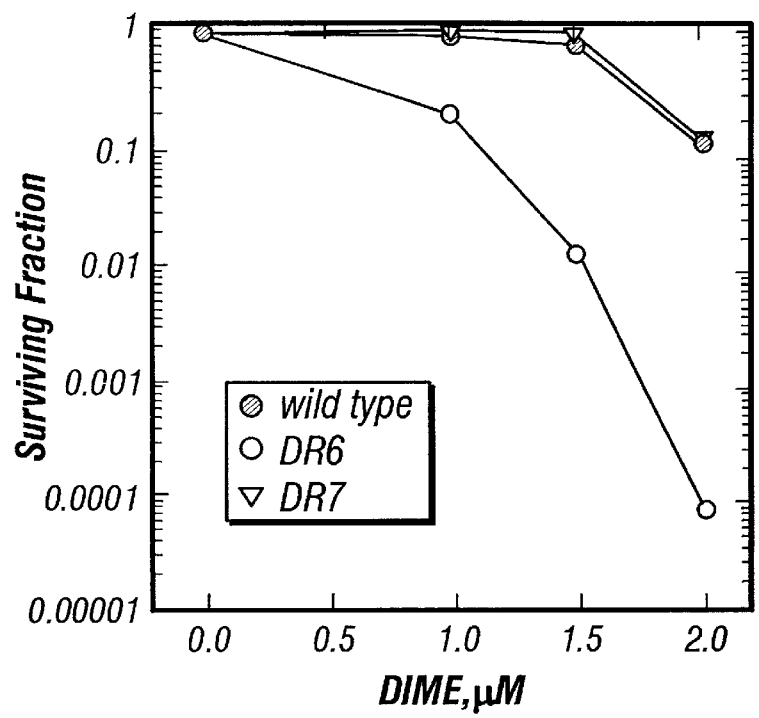
FIG. 8 indicates the sensitivity of wild type and DR-6 and DR-7 clones to DIME, assayed by colony formation.
Figure 9:
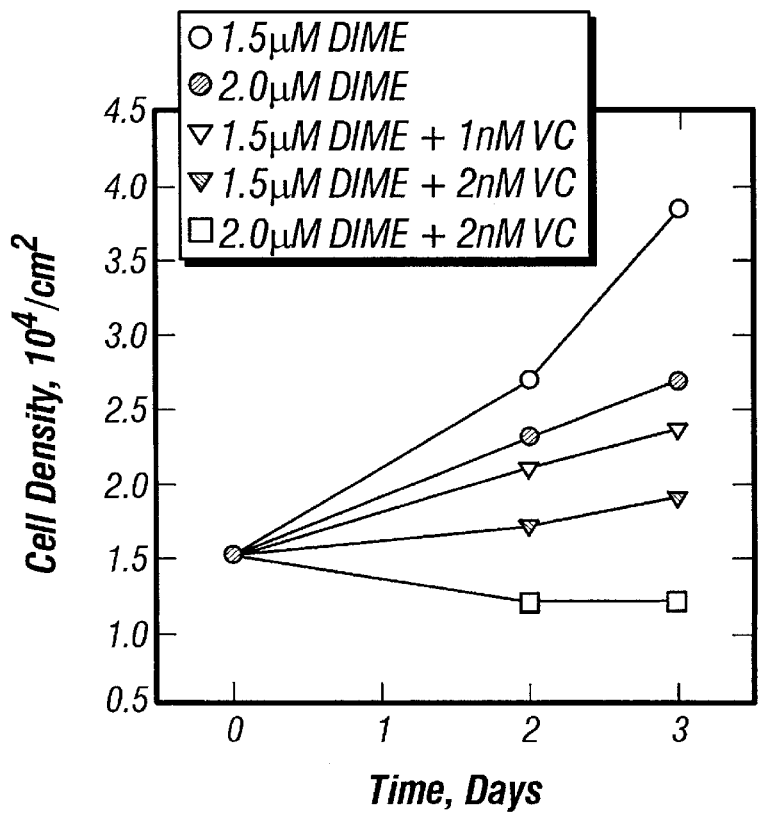
FIG. 9 demonstrates potentiation by vincristine (VC) on growth inhibition of DIME-tolerant cancer cells at various DIME concentrations.

$^1$H NMR spectrum (360 MHz) in DMSO-d6 (δ(ppm) values relative to TMS): 2.662 (3H, singlet), 3.775 (3H, singlet), 6.746 (2H, doublet, J=9.16 Hz, plus fine splitting), 6.957 (2H, doublet, J=9.33 Hz, plus fine splitting), 8.470 (2H, singlet).

c. MDA-MB-231 human mammary cancer cells were cultured and treated as reported previously by Mendeleyev et al., *International Journal of Oncology* 10:689–695 (1997) and Zhen et al., *International Journal of Oncology* 10:689–695 (1997). For the assay of cell growth kinetics cells, were seeded into $2cm^2$ wells (24-well plates) at a density of $8 \times 10^3/cm^2$ at the time of seeding. Vincristine (or vinblastine) and DIME (or DIPE) were added from DMSO dilutions (1–2 μl/ 500 μl culture mediim) either from separate drug solutions or for the construction of median effect plot (FIG. 1) from a pre-made mixture of both drugs (e.g. 0.75 μM DIME+2 nM vincristine) and simultaneous dilutions thereof (Chou et al. *Eur. J. Biochem.* 115: 207–216 (1981)). The cultures were incubated at 37° C. for 4 days and growth rates, leading to near confluency in drug-free controls, were monitored by cell counting in a haemocytometer after detachment by trypsin treatment Mendeleyev et al., *International Journal of Oncology* 10:689–695 (1997) and Zhen et al., *International Journal of Oncology* 10:689–695 (1997). Mathematical analysis of growth curves and median effects and isobolograms were carried out by published procedures (Chou et al. *J. Theor. Biol.* 65: 345–356 (1977), Chou et al. *Eur. J. Biochem.* 115: 207–216 (1981) and Chou et al. *Adv. in Enzyme Regulation* 22:27–55 (1984)) and error bars indicate SD=$\sqrt{\Sigma x^2 - (\Sigma x)^2}/n$ where X is the numerical results with n=3–5.

n−1 d. DIME-tolerant clones DR6 and DR 7 were isolated by incubation of cells in a mediim containing 1.5 μM DIME for 11 days. At that time surviving colonies were picked with the use of cloning rings and plated for growth in fresh mediim still containing 1.5 μM DIME. After two weeks of growth in the presence of drug the cells were aliquoted and frozen. For each experiment a vial of frozen cells was thawed, the cells were plated in the absence of drug, and incubated for 2–3 days in drug-free mediim. These cells were then used for experiments to generate survival and growth curves (FIGS. 8,9).

e. Colony formation was quantitated as reported by. Each colony of 50 cells is the outgrowth from one cell, plated 10 days before colony counting.

f. Determination of the binding constant for DIME-tubulin complex. A series of concentrations of [$^{14}$C]DIME (1.64 μM–28.6 μM) were incubated with 1 mg/ml bovine brain tubulin (10 μM) in 200 μl PK buffer (67 mM phosphate, 100 mM KCl, 10% DMSO, pH 6.8) for 1 hr at 37° C. After incubation, the reaction mixes were transferred onto 1 ml spin columns filled with Sephadex G50 equilibrated with the same buffer, then an additional 210 μl of PK buffer was added, followed by centrifugation for 10 seconds at 150×g. The exclusion volume containing the protein and the bound radioactive DIME was transferred into scintillation vials and the radioactivity was counted using Ecolume scintillation fluid. Because the DIME-protein association products may be falsified by DIME-Sephadex binding, corrections were made by varying the size of the Sephadex columns, and values were extrapolated to a zero-size column, to approach the true DIME-tubulin binding constant.

g. Caspase 3 assay. MDA 231 cells were grown for 3 days in the absence of drugs (control) or in the presence of 0.75 μM DIME, or in the presence of 2 nM vincristine, or in the presence of both drugs. After harvesting and washing the cells with PBS, they were lysed in a lysis buffer (10 mM HEPES, 5 mM DTT, 2 mM EDTA, 1 mM PMSF, 0.1% CHAPS, 20 μg/ml each of aprotinin, leupeptin, pepstatin, pH 7.4), and were frozen and thawed 3 times. The centrifuged supernatants of the cell extracts were assayed for caspase activity with the FluorAce Apopain Assay Kit (cat# 170-3130B, BioRad, Hercules Calif.) according to the manufacturer's suggestions. Each cell extract was incubated at room temperature with and without preincubation with the caspase inactivator DEVD-CMK. The difference of fluorescence was plotted against time. The fluorescence was calibrated with the fluorophore AFC.

Results

Kinetics of vincristine-DIME interactions: Interpretation of conventional isobolograms, consisting of plots of $I_{50}$ values of two drugs alone and in combination is valid only if it is proven kinetically that both drugs bind at mutually exclusive sites. As shown in FIG. 1, parallel lines are obtained when log $(1/f_v-1)$ values are plotted against log [DIME] or log [vincristine] or their combination, where $f_v$ is the inhibited growth rate. The virtually identical slopes obtained provide evidence of "mutually exclusive" cellular sites of DIME and vincristine.

Figure 2:
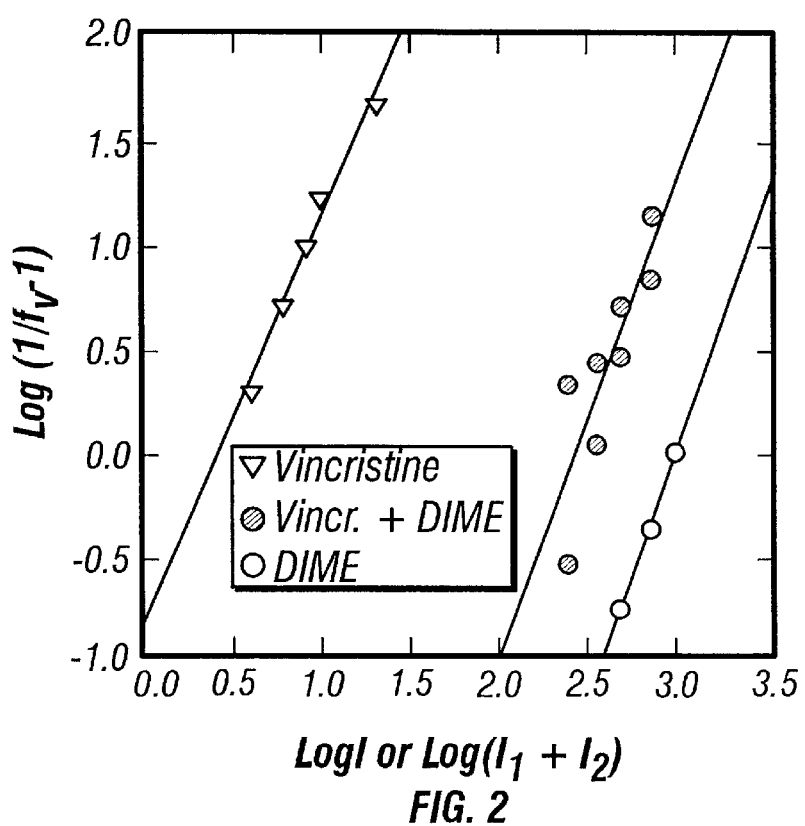
FIG. 2 represents an isobologram based on cell growth inhibition. The $I_{50}$ values were derived from cell counts in cell-growth experiments (see Methods).
Figure 3A:
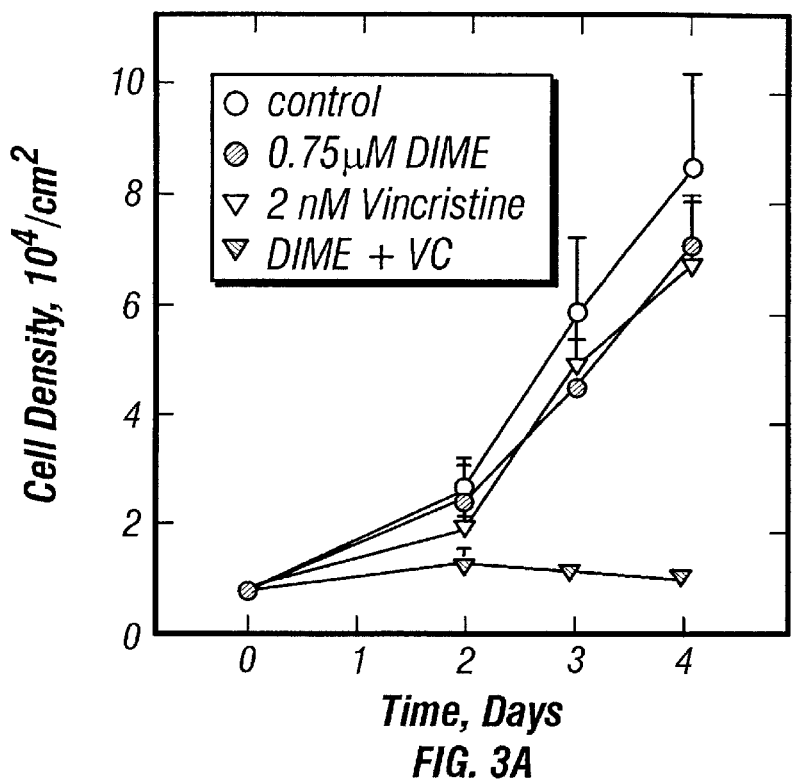
FIG. 3 represents (a) A potentiation of the growth inhibitory action of simultaneously added DIME and vincristine at a drug ratio of 0.75 μM DIME: 2 nM vincristine (see Methods). (b) same as (a) but DIME is replaced by DIPE.

Isobologram analysis of the combined action of DIME and vincristine is illustrated in FIG. 2, and it is evident that the action of the two drugs in combination exceed an additive effect, which is depicted by a concave curve, contrasting with additive action, which would display a straight line connecting the $I_{50}$ values for each drug alone (dotted line in FIG. 2). The experimentally obtained concave curve indicates mutual potentiation or synergy. It should be noted that these values were obtained by $I_{50}$ assays with near linear cell growth curves, thus conditions closely approximate criteria put forward by the "median" effect theory as explained by Chou et al., *Eur. J. Biochem.* 115:207–216 (1981) and Chou et al., *Adv. In Enzyme Regulation* 22:27–55 (1984)) that is based on the Michaelis-Menten kinetics. When isobolograms were constructed from results obtained by the effects of drugs on colony formation, determined after 10 days of cell growth (FIGS. 6–8), apparent additive effects may be observed (not shown). It is probable that the kinetics of colony formation which is the multiplication of one cell to a colony of 50 cells in 10 days is more complex than initial growth rates, thus $I_{50}$ values are not comparable in the colony forming tests with initial cell growth rates.

Figure 3B:
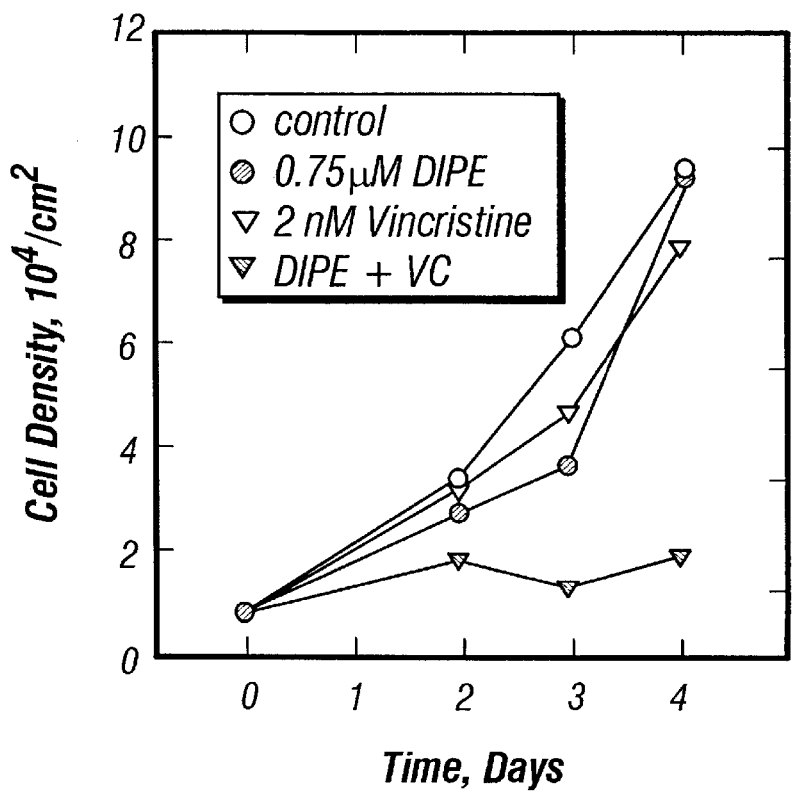

Potentiation of the effect of DIME by vincristine is illustrated in FIG. 3a, when by themselves ineffective concentrations of DIME (0.75 μM) and vincristine (1 or 2 nM) are combined and a complete growth inhibition is obtained. Growth rates of cells without drug and in the presence of 0.75 μM DIME or 2 nM vincristine as a single drug fall within SD values, implying a very large cooperative effect if both drugs are added in given proportion simultaneously. Nearly identical results were obtained when DIME was replaced by the non-hydrolyzable analog DIPE (FIG. 3b). The advantage of DIPE is evident from previous results (Mendeleye et al., *International J. of Oncology* 10:689–695 (1997)) that show esterase activity in certain tumor cells and we assume that trace DIME hydrolysis in other tumor cells cannot be strictly ruled out, thus DIPE is a more stable drug candidate.

Figure 4A:
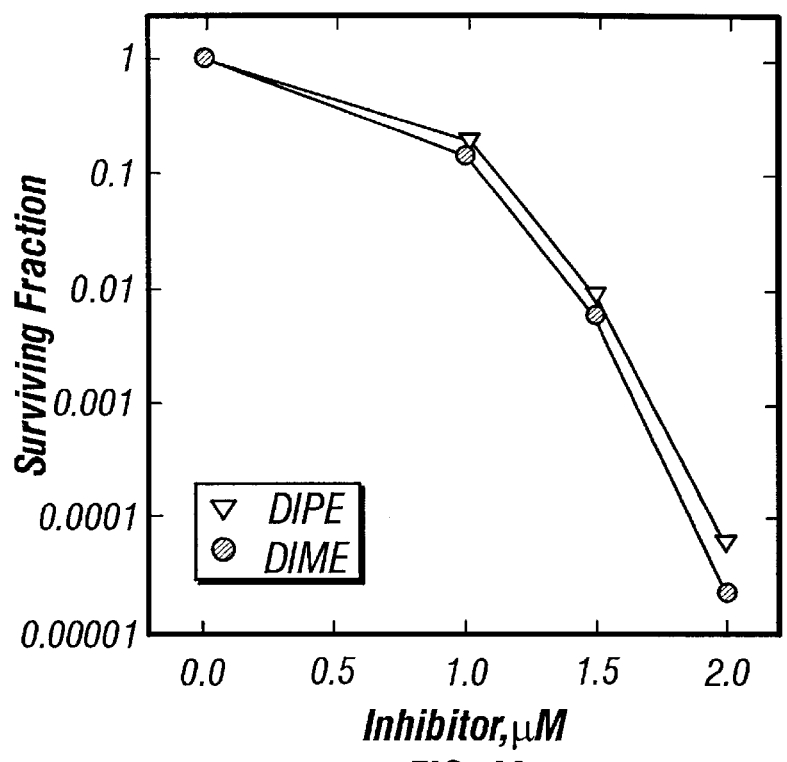
FIG. 4 demonstrates (a) Equivalent effectivity of DIME and DIPE as determined by their inhibitory potency on colony formation, assayed as reported by Mendeleyev et al., *International Journal of Oncology* 10:689–695 (1997). (b) Inhibitory effects of DIME and DIPE on the rates of polymerization of tubulin α+β. The optical tests were performed as reported by Buki et al., *International Journal of Oncology* 10:911–913 (1997).
Figure 4B:
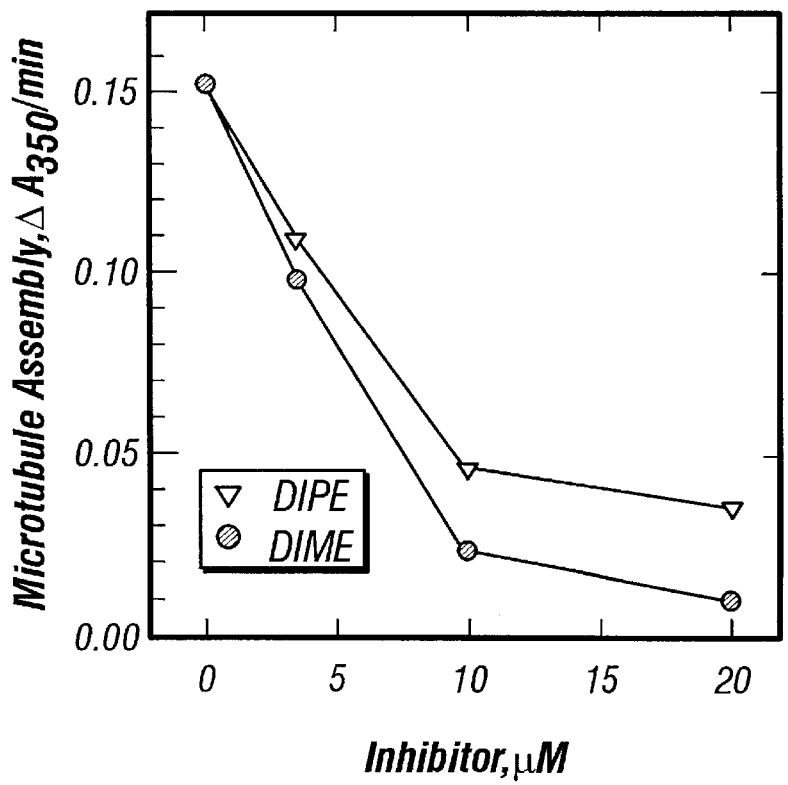
Figure 5A:
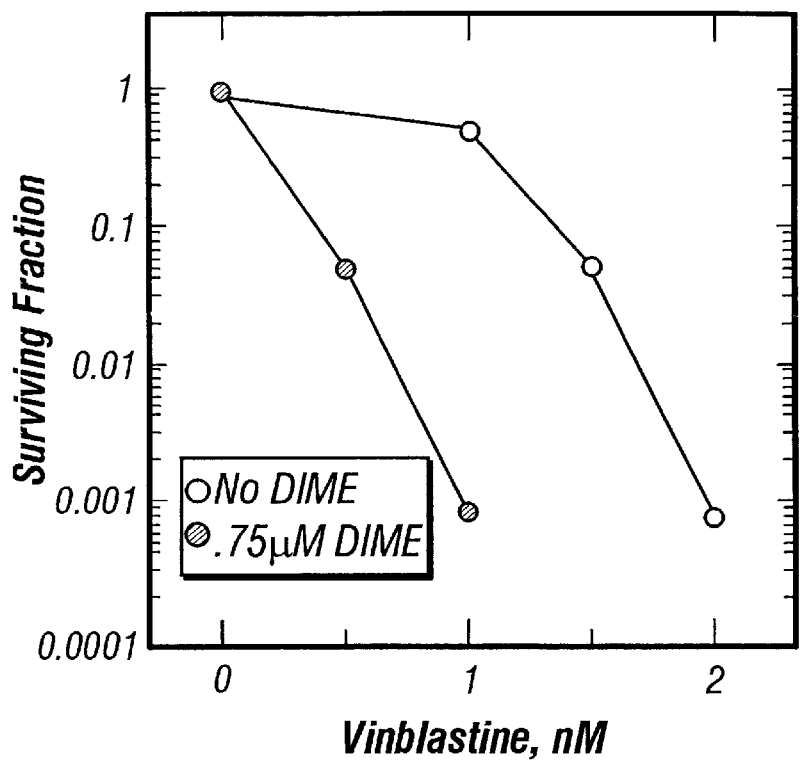
FIG. 5 demonstrates (a) The effect of varying concentration of vinblastine (abscissa) at 0.75 μM DIME concentration, that is kept constant, on cell killing, assayed by colony formation. (b) Same as (a) except the concentration of DIME is varied (abscissa) while vinblastine is kept constant at 1 nM.
Figure 5B:
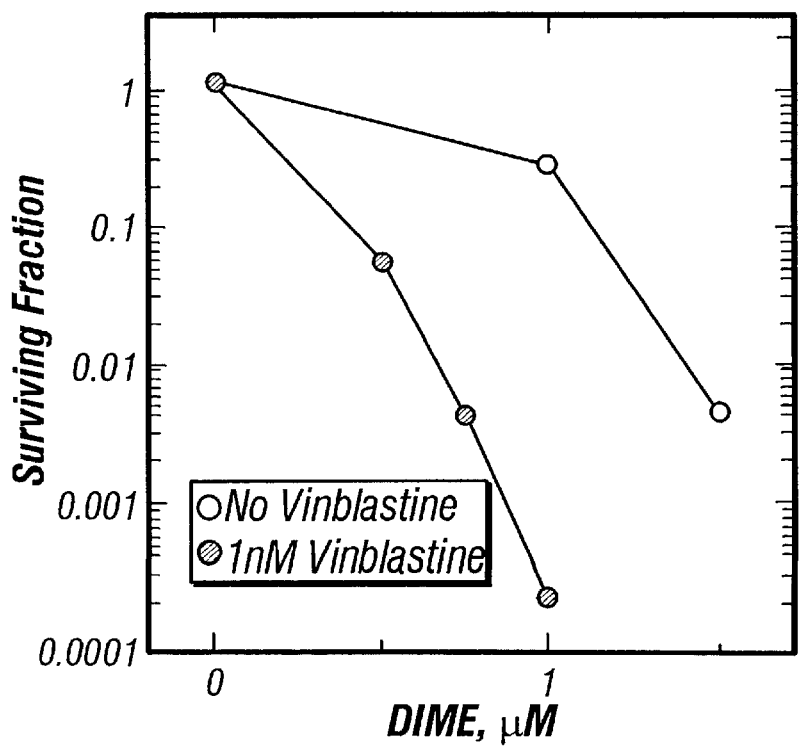

The equivalency of DIME and DIPE is also illustrated in FIG. 4a and 4b, where effects are shown on colony formation (FIG. 4a) and on the inhibition of the assembly of microtubules (FIG. 4b). The combined effects of vinblastine and DIME on colony formation are shown in FIG. 5a and 5b where drug combinations bring about a thousand fold increase in cell killing as compared to each drug alone.

Figure 6:
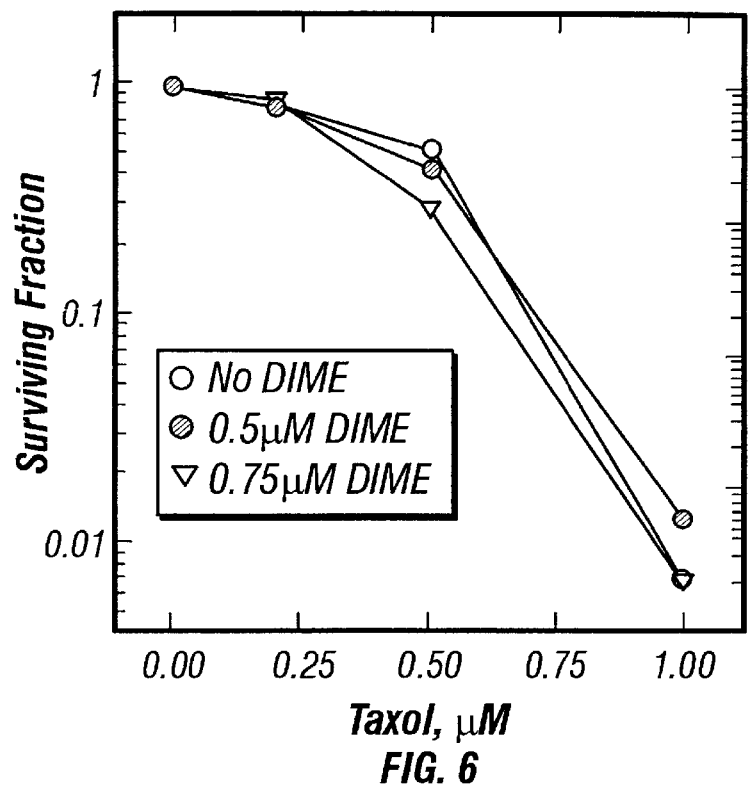
FIG. 6 demonstrates the absence of interaction between DIME and taxol, assayed by colony formation.

The absence of combined effect of taxol and DIME is in sharp contrast to DIME-vinca alkaloid combinations. As shown in FIG. 6 there is no apparent interaction between taxol and DIME on colony formation.

Figure 7:
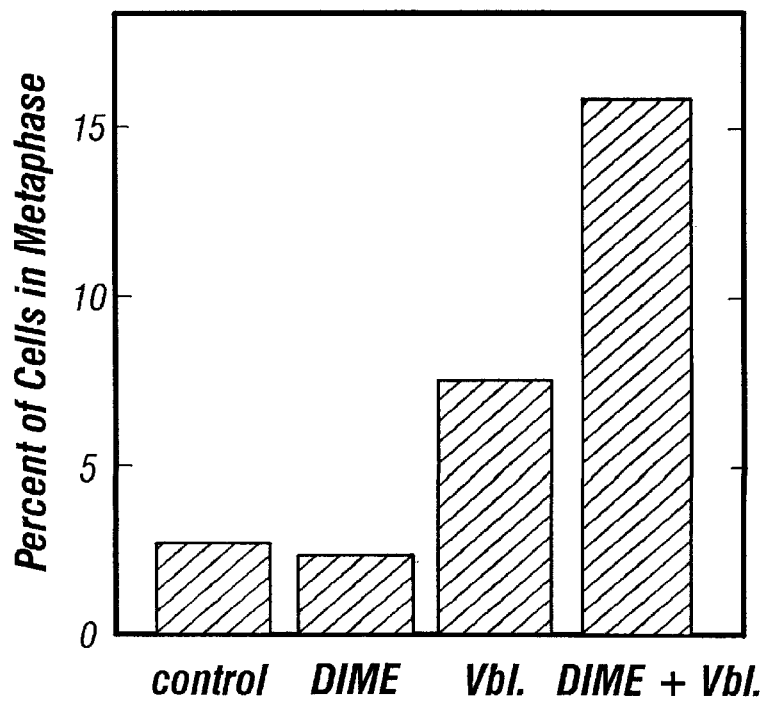
FIG. 7 demonstrates the combined effects of 0.75 μM DIME and 1 nM vinblastine on metaphase block. Metaphase was quantitated as reported by Mendeleyev et al., *International Journal of Oncology* 10:689–695 (1997).

As we have shown that DIME induces M-block (Id.) we determined the combined action of vinca alkaloids on metaphase arrest. Since vincristine and vinblastine were equivalent here we illustrate only DIME-vinblastine interaction on mitotic block. This is shown in FIG. 7, where only mean values are given (SD did not exceed ±20%).

Several naturally-occurring alkaloids obtained from *Vinca rosea* have demonstrated efficacy in treating malignancies. Examples of these include leurosine, vincaleukoblastine or vinblastine, leuroformine; leurosidine (vinrosidine) and leurocristine or vincristine; deoxy vinblastine "A" and "B"; 4-desacetoxyvinblastine; 4-desacetoxy-3-hydroxyvinblastine; leurocolombine and vincadioline. At least two of these alkaloids, vinblastine and vincristine, are now marketed as drugs for treating malignancies, especially leukemias and related diseases in humans.

MBA-MD-231 cells grown in the presence of 1.5 μM DIME (clones DR6, DR7) demonstrate that only marginal inhibition of colony formation occurs in DR6 and DR7 cells at concentrations of DIME which reduce colony formation by $10^3$ (FIG. 8) in the parent cell line. On the other hand as shown in FIG. 9, an increase of DIME concentration from the tolerated 1.5 μM to 2.0 μM depressed rates of cell growth by about 30%. Addition 1 or 2 nM vincristine to DIME-tolerant cells grown in 1.5 μM DIME remarkably inhibits cell growth, which is completely abrogated when 2 nM vincristine is combined with 2 μM DIME.

Since we found that nontumorigenic cells take up significantly less DIME than malignant counterparts (Id.) rates of DIME uptake were also assayed in cells that grew in the presence of 1.5 μM DIME. There was a 50% reduction of DIME uptake in the "DIME-tolerant" clones, grown in 1.5 μM DIME (results not shown). Moreover these cells have a prolonged doubling time.

Figure 10:
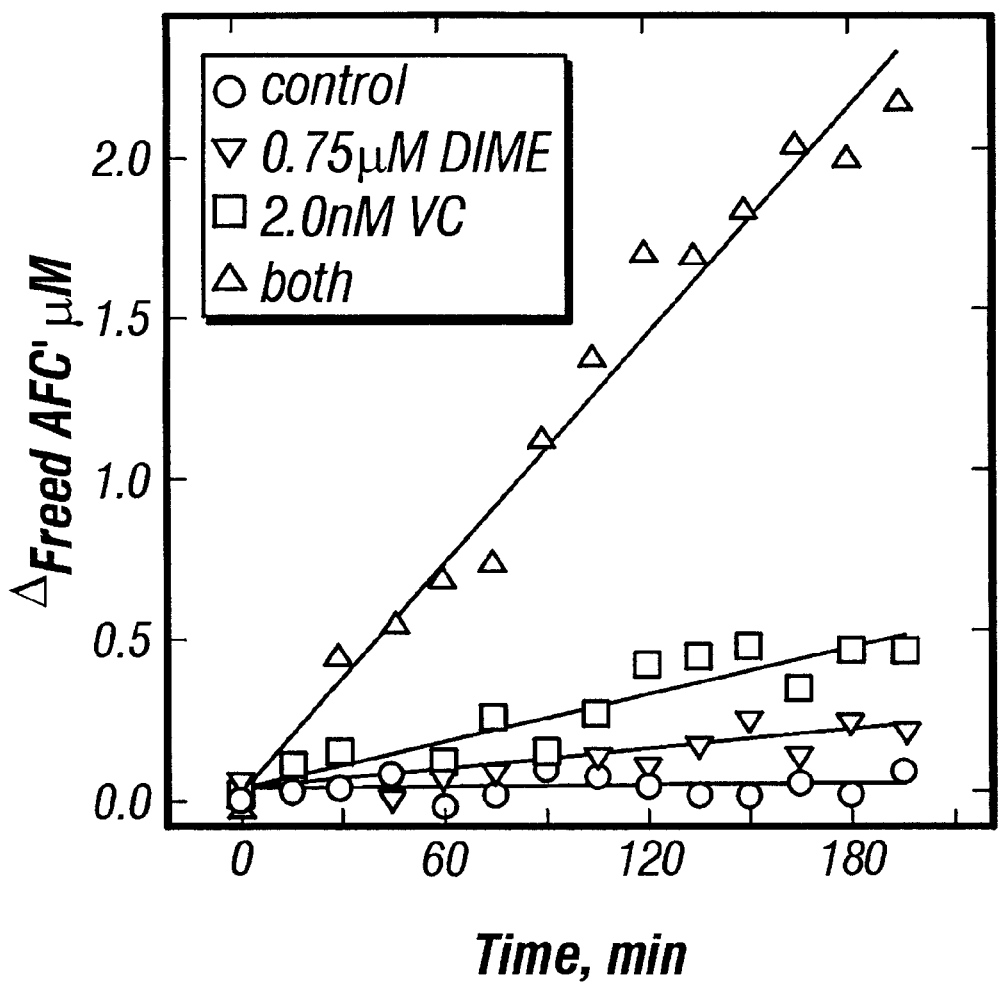
FIG. 10 demonstrates the activation of cellular caspase 3 by DIME and by vincristine alone and in combination.

An inordinately large potentiation of the effect of a drug mix (0.75 μM DIME, 2 nM vincristine) on cell growth correlated with a large potentiation of the activation of caspase 3 in cells. This is summarized in FIG. 10. Both drugs alone when incubated with cells induce a small rate of caspase 3 activity, but drug combination (0.75 μM DIME+2 nM vincristine) augments caspase 3 about to the same extent as this drug mix inhibits cell growth (FIG. 3a,b). Since we have shown that incubation of cells with DIME induces DNA breaks, activation of caspase 3 can explain drug-induced apoptosis. Action of caspase 3 can only be obtained when cells are incubated with drug combinations. Cell-free extracts do not show an increase in caspase 3 when treated with drugs (results not shown).

The foregoing written specification is considered to be sufficient to enable one skilled in the art to practice the invention. Indeed, various modifications of the above-described modes for carrying out the invention which are obvious to those skilled in the field of pharmaceutical formulation or related fields are intended to be within the scope of the following claims.

What is claimed is:

1. A method of inhibiting growth of tumor cells in a mammal comprising the step of administering a pharmaceutically effective amount of the combination of a diiodo thyronine analogue having no significant hormonal activity and a vinca alkaloid selected from the group consisting of leurosine, vincaleukoblastine, vinblastine, leuroformine, leurosidine, leurocristine, vincristine, deoxy vinblastine, 4-desacetoxyvinblastine; 4-desacetoxy-3-hydroxyvinblastine, dihydro vinblastine, leurocolombine, and vincadioline, sufficient to depress growth of the tumor cells sensitive to the combination, wherein the diiodo thyronine analogue has the formula:

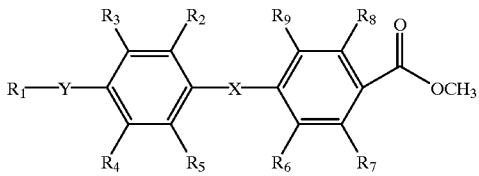

and pharmaceutically acceptable salts thereof, wherein:
X=O, S, CH$_2$, carboxy or absent;
Y=O or S;
R$_1$=methyl or ethyl;
R$_2$, R$_3$, R$_4$ and R$_5$ are independently selected from the group consisting of: H, (C$_1$–C$_4$) alkyl, (C$_1$–C$_4$) alkenyl, (C$_1$–C$_4$) alkynyl, hydroxyl, (C$_1$–C$_4$) alkoxy and halogen; and
R$_6$, R$_7$, R$_8$, and R$_9$ are independently selected from the group consisting of: H, (C$_1$–C$_4$) alkyl, (C$_{1-C4}$) alkenyl, (C$_1$–C$_4$) alkynyl, hydroxyl, (C$_1$–C$_4$) alkoxy, halogen, and NH$_2$;
wherein the combination of said vinca alkaloid and said diiodo thyronine analogue provides greater than an additive effect on inhibiting growth of the tumor cells sensitive to the combination.

2. A method of inhibiting growth of tumor cells in a mammal comprising the step of administering a pharmaceutically effective amount of the combination of a diiodo thyronine analogue having no significant hormonal activity and a vinca alkaloid selected from the group consisting of leurosine, vincaleukoblastine, vinblastine, leuroformine, leurosidine, leurocristine, vincristine, deoxy vinblastine, 4-desacetoxyvinblastine; 4-desacetoxy-3-hydroxyvinblastine, dihydro vinblastine, leurocolombine, and vincadioline, sufficient to depress growth of the tumor cells sensitive to the combination, wherein the diiodo thyronine analogue has the formula:

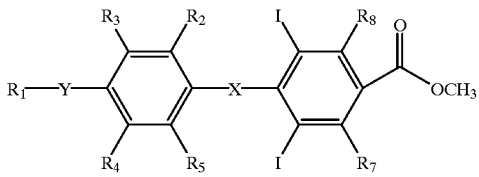

and pharmaceutically acceptable salts thereof, wherein:
X=O, S, CH$_2$, carboxy or absent;
Y=O or S;
R$_1$=methyl or ethyl;
R$_2$, R$_3$, R$_4$ and R$_5$ are independently selected from the group consisting of: H, (C$_1$–C$_4$) alkenyl, (C$_1$–C$_4$) alkynyl, hydroxyl, (C$_1$–C$_4$) alkoxy and halogen; and R$_7$ and R$_8$ are independently selected from the group consisting of: H, (C$_1$–C$_4$) alkyl, (C$_1$–C$_4$) alkenyl, (C$_1$–C$_4$) alkynyl, hydroxyl, (C$_1$–C$_4$) alkoxy, halogen, and NH$_2$;
wherein the combination of said vinca alkaloid and said diiodo thyronine analogue provides greater than an additive effect on inhibiting growth of the tumor cells sensitive to the combination.

3. The method according to claim 1, wherein the diiodo thyronine analogue is methyl 3,5-diiodo-4-(4'-methoxyphenoxy)benzoate.

4. The method of claim 1, wherein the diiodo thyronine analogue is selected from the group consisting of 1-[3,5-diiodo-4-(4'-methoxyphenoxy)-phenyl]-ethanone (DIPE) and 1-[3,5-diiodo-4-(4'-methoxyphenoxy)-phenyl]-1-propanone (DIPP).

5. The method according to any one of claims 2–4, and 7, wherein the diiodo thyronine analogue is administered in an amount effective to cause regression of the growth of tumor cells sensitive to the combination.

6. The method according to any one of claims 2–4, and 7, wherein the diiodo thyronine analogue is administered orally.

7. A method of treating carcinoma or sarcoma comprising the step of administering a pharmaceutically effective amount of a composition comprising a combination of a dijodo thyronine analogue and a vinca alkaloid selected from the group consisting of leurosine, vincaleukoblastine, vinblastine, leuroformine, leurosidine, leurocristine, vincristine, deoxy vinblastine, 4-desacetoxyvinblastine; 4-desacetoxy-3-hydroxyvinblastine, dihydro vinblastine, leurocolombine, and vincadioline, sufficient to depress growth of the carcinoma or sarcoma sensitive to the combination, wherein the diiodo thyronine analogue has the structural formula:

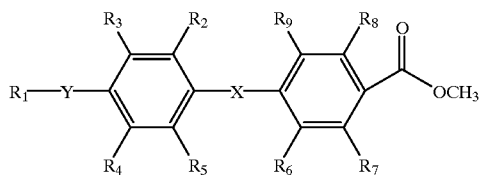

and pharmaceutically acceptable salts thereof, wherein:
X=O, S, CH$_2$, carboxy or absent;
Y=O or S;
R$_1$=methyl or ethyl;
R$_2$, R$_3$, R$_4$ and R$_5$ are independently selected from the group consisting of: H, (C$_1$–C$_4$) alkyl, (C$_1$–C$_4$) alkenyl, (C$_1$–C$_4$) alkynyl, hydroxyl, (C$_1$–C$_4$) alkoxy and halogen; and R$_6$, R$_7$, R$_8$ and R$_9$ are independently selected from the group consisting of: H, (C$_1$–C$_4$) alkyl, (C$_1$–C$_4$) alkenyl, (C$_1$–C$_4$) alkynyl, hydroxyl, (C$_1$–C$_4$) alkoxy, halogen, and NH$_2$;
wherein the combination of said vinca alkaloid and said diiodo thyronine analogue provides greater than an additive effect on treating the carcinoma or sarcoma sensitive to the combination.

8. The method according to claim 2 or 11, wherein said diiodo thyronine analog is methyl 3,5-diiodo-4-(4'-methoxyphenoxy-benzoate) and said vinca alkaloid is vincristine.

9. A pharmaceutical composition comprising a diiodo thyronine analogue and a vinca alkaloid selected from the group consisting of leurosine, vincaleukoblastine, vinblastine, leuroformine, leurosidine, leurocristine, vincristine, deoxy vinblastine, 4-desacetoxyvinblastine; 4-desacetoxy-3-hydroxyvinblastine, dihydro vinblastine, leurocolombine, and vincadioline, in an amount sufficient to depress growth of tumor cells, wherein the diiodo thyronine analogue has the structural formula:

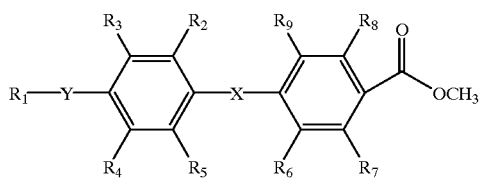

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen; and $R_6$, $R_7$, $R_8$ and $R_9$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, and $NH_2$;

wherein the combination of said vinca alkaloid and said diiodo thyronine analogue provides greater than an additive effect on inhibiting growth of the tumor cells sensitive to the combination.

10. A pharmaceutical composition according to claim 9, wherein the diiodo thyronine analogue is selected from the group consisting of methyl 3,5-diiodo-4-(4'-methoxyphenoxy)benzoate (DIME), 1-[3,5-diiodo-4-(4'-methoxphenoxy)-phenyl]-ethanone (DIPE) and 1-[3,5-diiodo-4-(4'-methoxyphenoxy)-phenyl]-1-propanone (DIPP).

* * * * *